(12) United States Patent
Dein

(10) Patent No.: US 10,307,574 B2
(45) Date of Patent: Jun. 4, 2019

(54) VARIABLE DIAMETER SURGICAL DRAINS AND SHEATHS

(71) Applicant: John R. Dein, Fair Oaks, CA (US)

(72) Inventor: John R. Dein, Fair Oaks, CA (US)

(*) Notice: Subject to any disclaimer, the term of this patent is extended or adjusted under 35 U.S.C. 154(b) by 999 days.

(21) Appl. No.: 13/759,826

(22) Filed: Feb. 5, 2013

(65) Prior Publication Data

US 2013/0218135 A1 Aug. 22, 2013

Related U.S. Application Data

(63) Continuation of application No. 12/485,651, filed on Jun. 16, 2009, now Pat. No. 8,403,913.

(60) Provisional application No. 61/132,119, filed on Jun. 16, 2008.

(51) Int. Cl.
*A61M 27/00* (2006.01)
*A61M 25/00* (2006.01)

(52) U.S. Cl.
CPC ........ *A61M 27/00* (2013.01); *A61M 25/0023* (2013.01)

(58) Field of Classification Search
CPC .................. A61M 25/0023; A61M 27/00
See application file for complete search history.

(56) References Cited

U.S. PATENT DOCUMENTS

| | | | |
|---|---|---|---|
| 3,823,720 A | 7/1974 | Tribble | |
| 4,141,364 A | 2/1979 | Schultze | |
| 4,398,910 A | 8/1983 | Blake et al. | |
| 4,402,684 A | 9/1983 | Jessup | |
| 4,553,959 A | 11/1985 | Hickey et al. | |
| 4,692,153 A | 9/1987 | Berlin et al. | |
| 4,738,666 A | 4/1988 | Fuqua | |
| 4,846,791 A | 7/1989 | Hattler et al. | |
| 5,158,545 A | 10/1992 | Trudell et al. | |
| 5,456,667 A | 10/1995 | Ham et al. | |
| 5,472,418 A | 12/1995 | Palestrant | |
| 5,624,395 A * | 4/1997 | Mikhail et al. | ............ 604/99.04 |
| 5,637,091 A | 6/1997 | Hakky et al. | |
| 5,674,240 A | 10/1997 | Bonutti et al. | |
| 5,827,243 A | 10/1998 | Palestrant | |
| 6,626,859 B2 | 9/2003 | Von Segesser | |
| 6,673,042 B1 | 1/2004 | Samson et al. | |
| 6,679,871 B2 | 1/2004 | Hahnen | |
| 6,709,427 B1 | 3/2004 | Nash et al. | |
| 7,300,429 B2 | 11/2007 | Fitzgerald et al. | |

(Continued)

*Primary Examiner* — Kai H Weng
(74) *Attorney, Agent, or Firm* — Rudy J. Ng; Bret E. Field; Bozicevic, Field & Francis LLP

(57) ABSTRACT

Surgical drains and methods for using the same for draining a body cavity are provided. Aspects of the surgical drains of the invention include an elongated structure having a proximal end and a distal end and a lumen configured to drain a substance from the body cavity. The distal end is configured to be placed in a body cavity and change in diameter when present in the body cavity from a first diameter to a second diameter that is smaller than the first diameter, where the change in diameter is mediated by a diameter-varying element. Aspects of the invention further include sheaths configured to be disposed around surgical drains, such as surgical drains of the invention, and methods of using the surgical drains and sheaths. The devices and methods of the invention find use in a variety of applications.

20 Claims, 29 Drawing Sheets

(56) References Cited

U.S. PATENT DOCUMENTS

| | | | |
|---|---|---|---|
| 2003/0004462 A1* | 1/2003 | Halpin | A61B 17/0057 604/99.04 |
| 2004/0006331 A1 | 1/2004 | Shchervinsky | |
| 2004/0078026 A1 | 4/2004 | Wagner | |
| 2004/0087905 A1 | 5/2004 | Breznock et al. | |
| 2004/0092956 A1 | 5/2004 | Liddicoat et al. | |
| 2004/0133226 A1* | 7/2004 | Buckman | A61B 17/3415 606/167 |
| 2005/0038408 A1 | 2/2005 | Von Segesser | |
| 2007/0021768 A1 | 1/2007 | Nance et al. | |
| 2007/0135795 A1* | 6/2007 | De Paulis | A61M 27/00 604/541 |

* cited by examiner

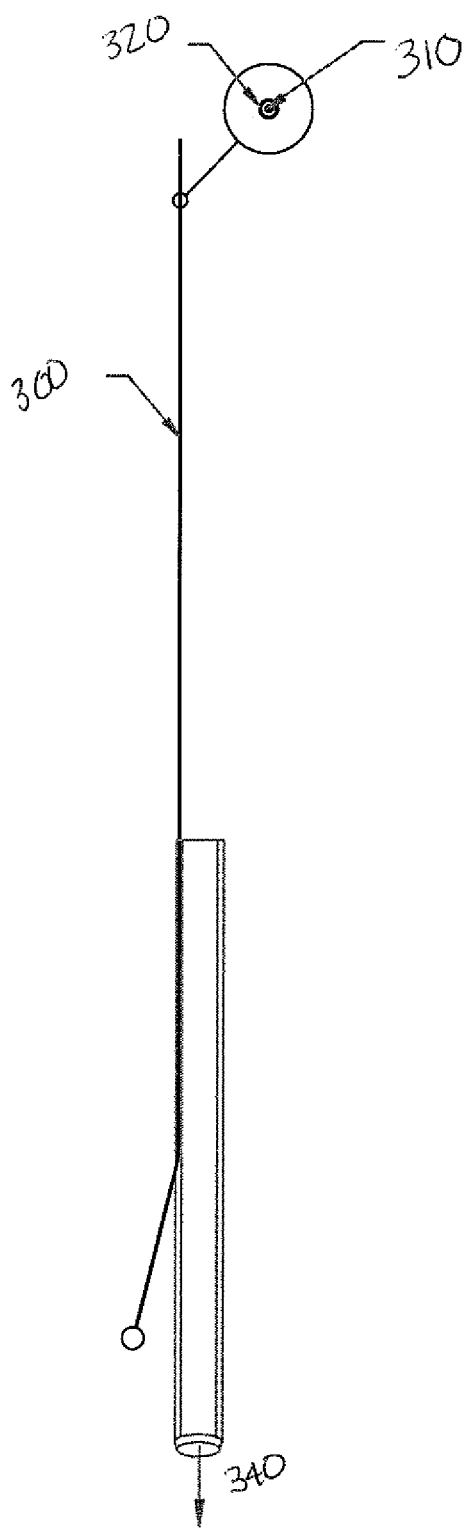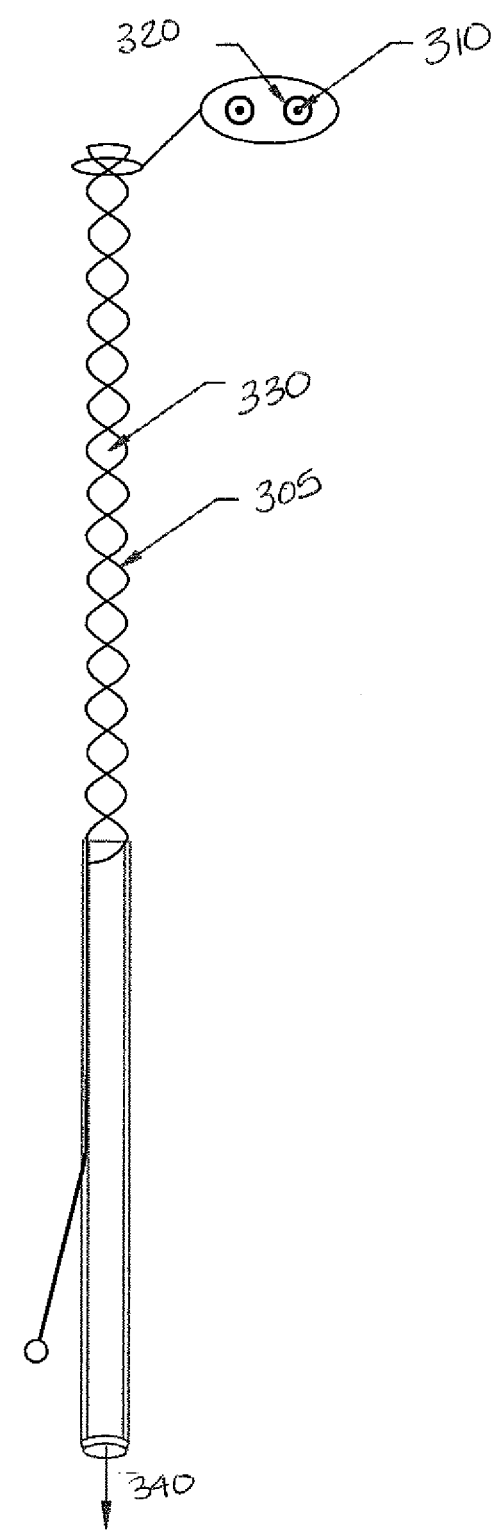
FIGURE 3A  FIGURE 3B
FIGURE 3

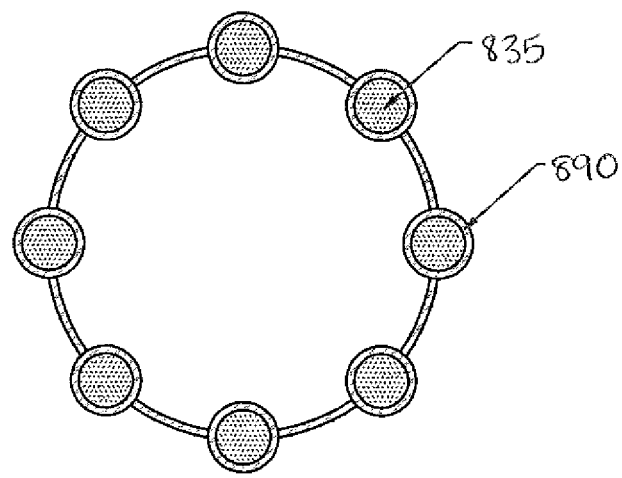
FIGURE 8A
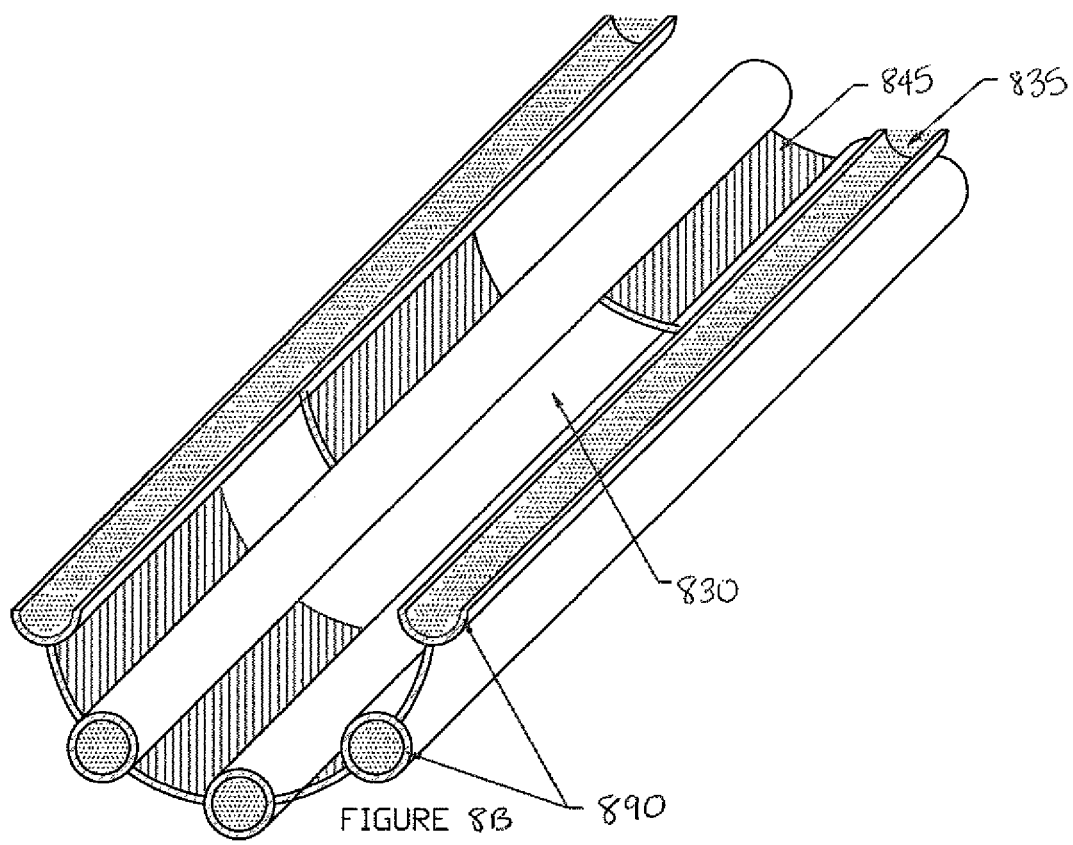
FIGURE 8B
FIGURE 8

VARIABLE DIAMETER SURGICAL DRAINS AND SHEATHS

CROSS-REFERENCE TO RELATED APPLICATIONS

Pursuant to 35 U.S.C. § 119 (e), this application claims priority to the filing date of the U.S. Provisional Patent Application Ser. No. 61/132,119 filed Jun. 16, 2008; the disclosure of which application is herein incorporated by reference.

INTRODUCTION

The nature of indwelling surgical drains, catheters, tubes or cannulas causes significant discomfort for the awake patient or animal. The discomfort is due to the contact of the drain or tube with internal structures, such as nerves, mucosal membranes, pleural, pericardial or peritoneal linings, skin or other tissues in contact with the drain tract while the drain is indwelling. For example, a chest tube left in the pleural cavity after cardiac or thoracic surgery is in contact with the visceral and parietal surfaces of the lung and chest wall, which are exquisitely sensitive. The tube usually also traverses the intercostal space, which is also quite sensitive.

A drain or chest tube is necessary after a surgical procedure in order to evacuate the air and body fluids and maintain the expansion of the lung required for respiration. The pleural space is normally maintained at a pressure slightly negative relative to atmospheric pressure by the body. While a chest tube or drain is in place, a slightly negative pressure can be maintained by suction applied via the drain. Maintenance of the negative pressure is one of the functions of a chest drain tube, in addition to the evacuation of air, body fluids, blood, clots and semi-solid and solid material.

FIG. 1 shows an example of a typical position of a thoracic chest tube drain 101 placed in the thoracic cavity of a human to evacuate air and body fluid. Also shown are fenestrations 102, which are holes within the chest tube to allow for the ingress of fluid and air into the central lumen of the tube. Drainage of the chest cavity using this type of chest tube has been employed for at least a century, with tubes constructed of various materials such as rubber, plastic, polymers, silicone, etc. When the chest tube is withdrawn, the hardness of the drain 101 and the sharp edges of the fenestrations 102 cause pain via contact with the tissues in multiple places including at the lining around the lungs (the visceral pleura), the lung lining at the chest wall (the parietal pleura), the intercostal space, adjacent nerves, and the skin. The indwelling nature of the drain and the need for rapid withdrawal of the chest tube to prevent air from entering via the tract of the drain causes significant pain, requiring intravenous or other narcotic pain relief.

With the aid of pain medications, patients can adjust to the discomfort of an indwelling tube for the several days the drains are needed, but then it is necessary to remove the drain relatively quickly so that no air is allowed into the thoracic cavity during removal. The relatively rapid withdrawal of chest drains or other functioning tubes from the thoracic cavity or other body cavities or organs tends to be a relatively painful experience for the patient. The pain is not so severe, however, to warrant the risks and expense of general anesthesia, nor is it practical to anesthetize via external injection the entire length of the tissue tract in contact with the tube to be removed.

Therefore, there is a need for improved surgical drains and methods for using surgical drains. There is a need for surgical drains which can provide a large area for effective therapeutic drainage of a body cavity during use, with the ability to significantly decrease the diameter of the surgical drain prior to removal of the drain from the body cavity. It would be a significant improvement in the patient's post-procedural experience to be able to decrease the pain experienced by a patient while the drain is indwelling, and during removal of the surgical drain.

SUMMARY

Surgical drains and methods for using the same for draining a body cavity are provided. Aspects of the surgical drains of the invention include an elongated structure having a proximal end and a distal end and a lumen configured to drain a substance from the body cavity. The distal end is configured to be placed in a body cavity and change in diameter when present in the body cavity from a first diameter to a second diameter that is smaller than the first diameter, where the change in diameter is mediated by a diameter-varying element. Aspects of the invention further include sheaths configured to be disposed around surgical drains, such as surgical drains of the invention, and methods of using the surgical drains and sheaths. The devices and methods of the invention find use in a variety of applications.

BRIEF DESCRIPTION OF THE FIGURES

FIGS. 3A and 3B provide a view of an embodiment of a surgical drain with a diameter-varying element, according to an embodiment of the invention.

FIGS. 8A and 8B provide a detailed view of another embodiment of a surgical drain with diameter-varying elements in the form of one or more balloons, according to an embodiment of the invention.

DETAILED DESCRIPTION

Figure 1:
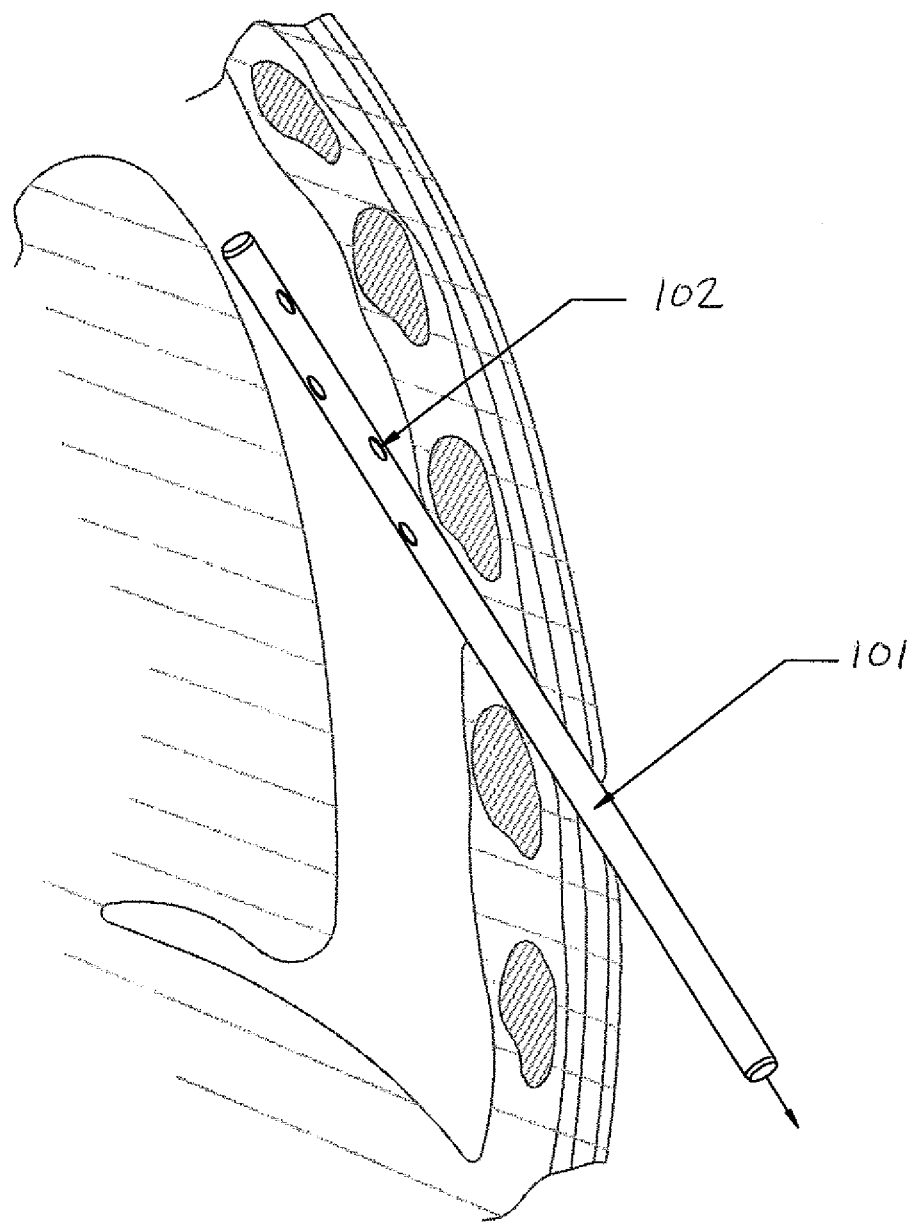
FIG. 1 provides a view of a prior art chest tube placed in a thoracic cavity.

Surgical drains and methods for using the same for draining a body cavity are provided. Aspects of the surgical drains of the invention include an elongated structure having a proximal end and a distal end and a lumen configured to drain a substance from the body cavity. The distal end is configured to be placed in a body cavity and change in diameter when present in the body cavity from a first diameter to a second diameter that is smaller than the first diameter, where the change in diameter is mediated by a diameter-varying element. Aspects of the invention further include sheaths configured to be disposed around surgical drains, such as surgical drains of the invention, and methods of using the surgical drains and sheaths. The devices and methods of the invention find use in a variety of applications.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the module of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

In further describing various aspects of the invention, the surgical drains and methods of their use will be described first in greater detail, followed by a review of sheaths of the invention and their use.

Surgical Drains

Surgical drains according to certain embodiments of the invention are devices that are configured to drain a substance from a body cavity. The surgical drains are configured to have a larger diameter when present in the body cavity, and change to a smaller diameter prior to removal from the body cavity. The surgical drains can also be used with a sheath configured to be disposed around the surgical drain. The subject devices and methods can be used in percutaneous, minimally invasive surgical, open surgical, or other interventional procedures.

Embodiments of the surgical drains include an elongated structure with a proximal and a distal end, and a lumen configured to drain a substance from a body cavity. In the discussion below, both the terms "elongated structure", "surgical drain of the subject invention", and "subject surgical drain" will be used to refer to a surgical drain of the subject invention. The elongated structure includes a distal end configured to be placed in a body cavity, such as a thoracic body cavity, and change in diameter when present in the body cavity from a first diameter to a second diameter that is smaller than the first diameter. The change in diameter of the distal end of the elongated structure is mediated by a diameter-varying element, described further below. The proximal end of the elongated structure is configured to be outside of the body when the distal end is present in the body cavity.

The elongated structure of the subject invention is an element that can drain a fluid, e.g., a liquid, air, etc., from a body cavity. The body cavity can include, but is not limited to, any body cavity in need of draining, such as a thoracic body cavity, which includes a body cavity in the chest including a pleural body cavity or a pericardial cavity, an abdominal body cavity, a gastrointestinal body cavity, a pelvic body cavity, a genitourinary body cavity, a cavity in the brain or spinal cord, a cavity in an extremity such as an arm or leg, etc. Further, the body cavity can be an anatomical or "natural" body cavity, e.g., the pleural space, or peritoneal space, or it can be a surgically-created or disease-created body cavity, e.g., an abscess cavity. In some embodiments, the body cavity can be a cavity in a solid organ, (e.g., liver, bone, etc.) In some embodiments, the body cavity can be a hollow organ, or an organ with a lumen, such as a urethra, a ureter, a portion of the intestine, the esophagus, the trachea, a bronchial tube.

In some embodiments, the elongated structure of the subject invention can be positioned to reach a body cavity by passing through an anatomical, or natural body tract or orifice. By natural orifice is meant an opening in the body that is part of a normally present anatomical structure, which can include but is not limited to the mouth, urethra, anus, vagina, etc. In other embodiments, the elongated structure of the subject invention can be positioned to reach a body cavity by passing through an artificial tissue tract. By artificial tissue tract is meant any tissue tract that is not naturally present in the body, such as a tract created through a chest wall, an abdominal wall, an extremity, etc. An artificial tissue tract can include a tract that has been created in the body, such as an iatrogenic tract, i.e., a tract created for a surgical procedure, or placement of a surgical drain, catheter, tube, etc. An artificial tissue tract can also include a tract that has been created in the body by a disease process, such as infection, inflammation, or tumor, and can include processes such as a draining abscess cavity, a fistula, a tract created by a tumor or other growth, etc.

The dimensions of the elongated structure will vary depending on the physical location of the surgical drain, and the substance that needs to be drained. For example, a surgical drain configured to drain a thoracic body cavity can be longer than a surgical drain configured to drain a urinary bladder. Similarly, an elongated structure configured to drain a thoracic body cavity can have a larger diameter than an elongated structure configured to drain a urinary bladder. In some instances, the length of the elongated structure may range from less than 1 cm to more than 300 cm, such as from 5 cm to 90 cm, and including from 15 cm to 30 cm.

The lumen in the elongated structure is configured to drain a substance from a body cavity. As such, the lumen can drain substances from any body cavity as disclosed above. Substances which can be drained, include, but are not limited to, fluids produced by the body including pleural fluid, pericardial fluid, blood, serous fluid, infected fluid, urine, cerebrospinal fluid, joint fluid, lymph, gastrointestinal fluid, etc. Substances which can be drained can also include fluids which have been introduced into the body or body cavity, such as saline, or pharmaceutical agents, etc. As such, the inner diameter of the lumen will vary depending on the physical location of the surgical drain. For example, an elongated structure configured to drain blood that may contain clots, or infected fluid, or bowel contents, can have a larger diameter than an elongated structure configured to drain a fluid such as air. In some embodiments, there can be more than one lumen, such as two or more, or three or more. In some embodiments, the drainage lumen is a central lumen. In other embodiments, there can be peripheral lumens. In some embodiments, there can be a central lumen and peripheral lumens around the central lumen. In some embodiments, the central lumen can be divided into compartments to form multiple lumens, such as with a central spline, discussed further below. In some instances, the inner diameter of the elongated structure may range from less than 1 mm to more than 5 cm, such as from 3 mm to 2 cm, and including from 5 mm to 10 mm.

The cross-sectional configuration of a surgical drain of the invention can be any suitable shape, such as round, oval, an oval shape with opposite pointed ends or flanges (e.g., a "football" shape), rectangular, square, cross, etc. The drain can also be formed into any suitable configuration, as long as it defines a lumen of suitable configuration. Drain configurations of interest include, but are not limited to: linear, spiral, coil, double helix, etc. In some embodiments the entire drain has the same configuration. In other embodiments, at least a portion of the drain may have a different configuration, e.g., a spiral configuration in one segment of the drain, and a linear configuration in another segment of the drain. In some embodiments, the entire drain has the same diameter. In other embodiments, at least a portion of the drain has a different diameter from the remainder of the drain, e.g., a smaller diameter than the remainder of the drain. In some embodiments, where the surgical drain has a branched configuration, discussed further below, the drain can have different diameters in different portions of the drain. For example, the proximal main portion of the surgical drain may have a larger diameter than the limbs, or branching portions of the drain.

The elongated structure has a distal end that is configured to be placed into a body cavity. In some embodiments, the distal end of the elongated structure can be placed into a body cavity during an open surgical procedure. A body cavity that is exposed during an open surgical procedure can be referred to as an "open body cavity". In other embodiments, the distal end of the elongated structure can be placed into a body cavity during a minimally invasive procedure (e.g., with an endoscope), or can in some embodiments be inserted percutaneously. The methods of placing the elongated structure in the body are discussed further below.

In some embodiments (e.g., in embodiments where the elongated structure is inserted percutaneously or with a minimally-invasive procedure), the elongated structure may be configured to have a smaller diameter prior to insertion, and assume a larger diameter when present in the body cavity.

The elongated structure has a proximal end that is configured to be outside of the body when the distal end is present in the body cavity. The proximal end of the elongated structure is configured to be connected to a drainage apparatus, such as a chest drain, or drainage bag, e.g., in the case of a urinary drain. In some embodiments, the proximal end is configured to be connected to a suction device. In some embodiments, the proximal end may further include a valve, such as a valve to prevent body fluids from flowing back into the body, and also to prevent the entry of air from the environment, or contamination of the body cavity from the environment.

Drains are made of any suitable material, including but not limited to: silicone, polymers, thermoplastic elastomers, plastic, rubber, biodegradable material, metals, alloys, materials which can change configuration or diameter or rigidity with application of ultraviolet light, or other form of electromagnetic energy, changes in temperature, for example, or any other suitable material, and combinations or mixtures thereof. In some embodiments, the material of the surgical drain is "preformed". By "preformed" is meant that the tubing is constructed of a material which allows the drain to have a preferred configuration, such as a spiral shape. A "preformed" shape may be achievable by polymers whose shape is determined by temperature, light of any wavelength, or other energy source.

The surgical drain of the subject invention can include a diameter-varying element, which is an element that can significantly change the diameter of the subject surgical drain. In addition to the ability to change the diameter of a surgical drain, the diameter-varying element can provide hoop strength. By hoop strength is meant the ability of a drain or tube to withstand pressure, bending or crushing forces. The diameter-varying element can change the surgical drain of the subject invention from a larger diameter, which is referred to as an "expanded" state, to a smaller diameter, which can be referred to as a "collapsed" state. By "significantly change the diameter" of the surgical drain is meant a change in diameter of at least 20%, such as at least 30%, or at least 40%, or more than 50%, more than 70%, more than 80%, more than 90%, or more than 99% etc. In some embodiments, the significant change in diameter can be a decrease in diameter, and in some embodiments, the significant change in diameter can be an increase in diameter.

The diameter-varying element can be a wire, a balloon filled with a fluid, or a central spline, which embodiments are discussed further below. As such, the diameter-varying element is an element that can be inserted into or removed from a surgical drain (e.g., a wire), or it can be an element that is altered when present in the surgical drain (e.g., a balloon that is filled with a liquid). As such, the diameter-varying element can be present in a surgical drain when the drain is placed in a body cavity, or the diameter-varying element can be placed into a surgical drain after the drain has been placed in a body cavity.

For example, in some embodiments, the diameter-varying element is an element that maintains the surgical drain in a larger diameter (e.g., a preformed wire), which decreases to a smaller diameter once the diameter-varying element is removed. In other embodiments, the diameter-varying element is an element that can change the diameter of a surgical drain from a larger diameter to a smaller diameter (e.g., a straight wire inserted into preformed spiral tubing) once the diameter-varying element is inserted. In yet another embodiment, the diameter-varying element is altered when present in a surgical drain to decrease the diameter of the surgical drain before removal (e.g., a balloon that can have the air removed). In some embodiments, the alteration or change in a diameter-varying element can be controlled by remote means, such as with a radiofrequency or other electromagnetic signal, magnetic induction, etc. or automatic means, such as with a processor, etc.

In some embodiments, there can be more than one diameter-varying element in an elongated structure (e.g., more than one wire, such as two or more, or three or more, etc.). In some embodiments, there can be more than one type of diameter-varying element in an elongated structure (e.g., a wire and a balloon). In some embodiments, there can be a combination of diameter-varying elements in an elongated structure. For example, an elongated structure can have a central spline, which can further include balloons integrated into the central spline.

In some embodiments, the cross-sectional configuration of a surgical drain of the invention can change in cross-sectional configuration by a mechanical change in a diameter-varying element (e.g., one or more wires, or a central spline, etc.) A mechanical change can include shortening or lengthening of a diameter-varying element, or winding, unwinding, twisting, untwisting, etc. of a diameter-varying element. In some embodiments, devices such as a slide, or a lock, a clip, etc., can be used to hold a diameter-varying element in a particular configuration. For example, one or more wires in the wall of an elongated structure can be mechanically shortened such that the wires define a larger cross-sectional area by "bowing". The elongated structure can be held in the larger diameter configuration while in a body cavity by using a clip, for example, to hold the wires in the larger diameter configuration. In another example, a diameter-varying element such as a central spline can be "wound" or "unwound" such that the central spline changes in cross-sectional configuration, e.g., from a tight spiral in the "wound" configuration, to a looser spiral in the "unwound" configuration. A central spline in the "wound" configuration can also have a smaller diameter than a central spline in the "unwound" configuration. In some embodiments, the alteration or change in a central spline can be controlled by remote means, such as with a radiofrequency or other electromagnetic signal, magnetic induction, etc. or automatic means, such as with a processor, etc.

The diameter-varying element, when present, may or may not be integrated with the elongated structure. By integrated is meant that the diameter-varying element cannot be separated from the elongated structure without irreparably altering the elongated structure. Examples of integrated configurations are where the diameter-varying element is a balloon integrated into the wall of the elongated structure, e.g., as described in greater detail below. Examples of non-integrated configurations are where the diameter-varying element is a wire which can be separated from the elongated structure without comprising the elongated structure.

The diameter-varying element has a length sufficient to extend at least along the portion of the surgical drain that is inside the body cavity, such that the diameter-varying element provides a segment of the distal end of the surgical drain which can significantly change in diameter when present in the body cavity. For example, in certain embodiments, the diameter-varying element is present in the distal one third of a surgical drain. In some embodiments, the diameter-varying element is present in the distal half of a surgical drain. In some embodiments, the diameter-varying element is present along the entire length of the surgical drain. Therefore, the length of the diameter-varying element may vary, ranging in some instances from less than one cm to 300 cm, such as from 5 cm to 90 cm, and including from 15 cm to 30 cm.

In some embodiments, the diameter-varying element is present in the surgical drain when the surgical drain is initially placed in a body cavity to be drained. In other embodiments, the diameter-varying element is inserted into the surgical drain after the surgical drain has been placed into body cavity to be drained. Therefore, in some embodiments the diameter-varying element is present when the elongated structure is initially placed in the body cavity, and in some embodiments, the diameter-varying element is inserted into the elongated structure after the elongated structure has been placed in the body cavity.

The surgical drain of the subject invention further includes a "wall" portion, and a "core" portion. By "wall portion" of the surgical drain is meant the portion of the elongated structure which surrounds the drainage lumen, such that the wall surrounds the longitudinal axis of the drainage lumen. In some embodiments, therefore, the "wall" can have a cylindrical configuration. In some embodiments, the elongated structure can have a wall that defines more than one lumen, for example, the "wall" can have a "cross" configuration, with a lumen in the center of the cross. In some embodiments, therefore, the "wall" can surround a central drainage lumen, and can also define additional peripheral lumens around the central lumen with portions of the wall that extend in a perpendicular orientation to the long axis of the elongated structure, (e.g., "arms" of the cross, as described further below). The walls of the peripheral lumens can therefore be partially formed by the body tissue which surrounds the structure.

By "core" of the surgical drain is meant the portion of the elongated structure in the center of the drainage lumen, such that the longitudinal axis of the core is parallel with the longitudinal axis of the drainage lumen. The elongated structure of the subject invention can therefore include a wall portion and a core portion.

In some embodiments, the diameter-varying element is present in the wall portion of the elongated structure. In this embodiment, the elongated structure can have one or more fenestrations in the wall to allow for drainage of body fluids through the wall of the elongated structure. In other embodiments the "wall" can have a spiral configuration. In this embodiment, the "wall" of the elongated structure may be viewed as a support, in that the "wall" is not a continuous wall, but rather is a support structure. In such embodiments, once the elongated structure is placed in a body cavity, the walls are partially formed by the body tissue which surrounds the structure. For example, the "wall" of the elongated structure may be formed of tubing in a spiral configuration, which may have a diameter-varying element inside the tubing (e.g., a wire). In some embodiments, the diameter-varying element is present in the core portion of the elongated structure. By "core portion" of the surgical drain is meant the portion of the elongated structure in the center of the drainage lumen, such that the longitudinal axis of the core is parallel with the longitudinal axis of the drainage lumen.

Figure 2:
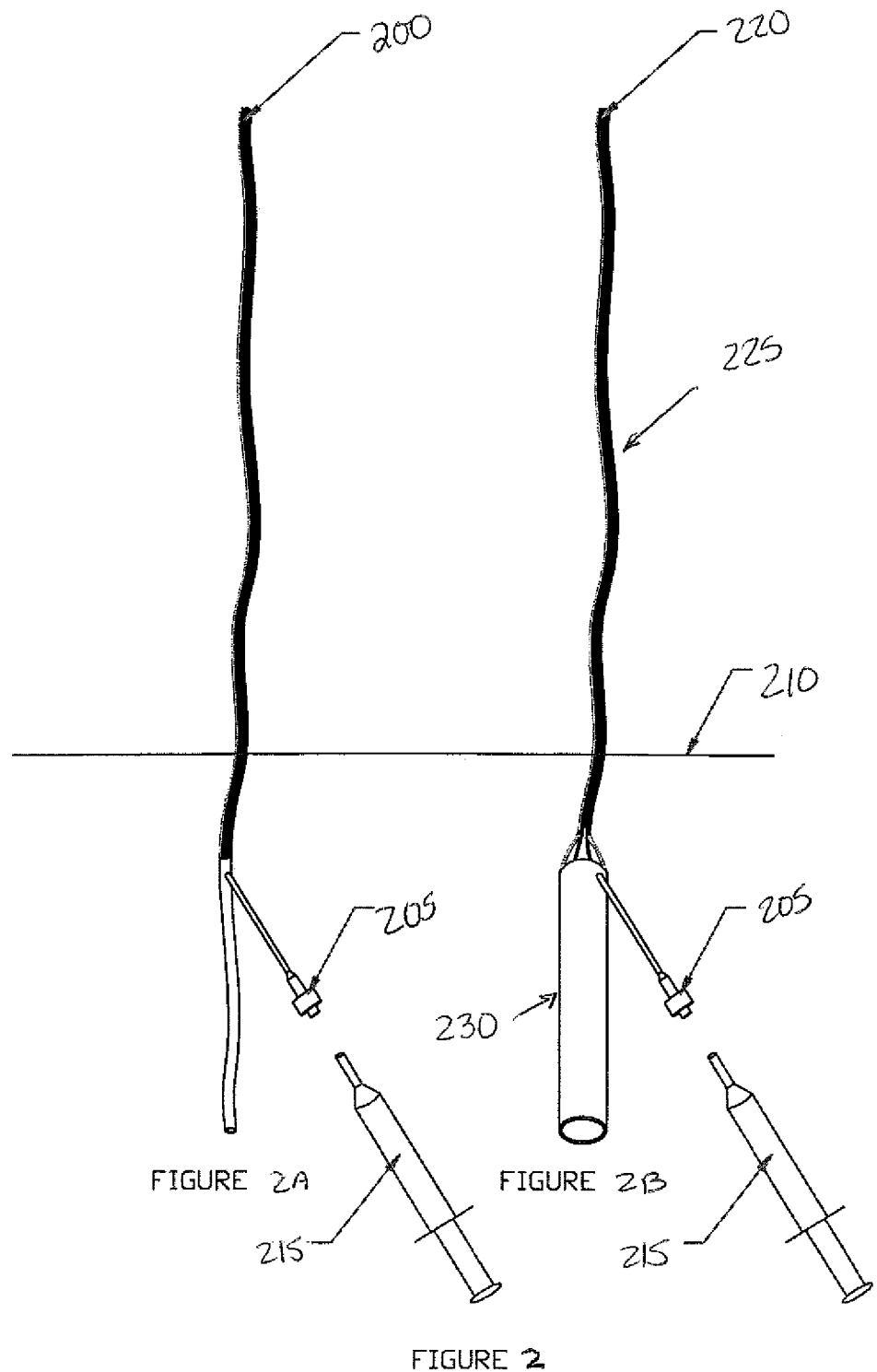
FIGS. 2A and 2B provide views of surgical drains, according to embodiments of the invention.

An embodiment of a surgical drain of the subject invention is shown in FIGS. 2A and 2B. FIG. 2A depicts a surgical drain 200 where the diameter has been decreased throughout the entire length of the surgical drain. In this embodiment, surgical drain 200 includes a diameter-varying element along the entire length of the surgical drain. For example, surgical drain 200 may include balloons in the wall inflated with air. Once the air is removed from the balloons, the diameter is no longer supported by balloon inflation or other mechanism, and is now ready to be withdrawn from the patient. In this example, the entire surgical drain is in the collapsed state, preventing any ingress of atmospheric air via the surgical drain itself, which traverses the skin and subcutaneous tissues 210.

FIG. 2B shows another embodiment of surgical drain of the subject invention 220. In this embodiment, the diameter of the distal portion of the surgical drain has been reduced, while the wall of the proximal portion 230 of the subject surgical drain is constructed of a rigid material surrounding the lumen of the drain that maintains its diameter. The proximal portion 230 with a fixed larger diameter facilitates connection to other devices, for example, a suction device, as discussed further below. In this embodiment, the surgical drain 220 includes a diameter-varying element in only the distal end of the diameter-varying element, e.g., the distal two-thirds of the surgical drain. In this example, therefore, only the distal portion of the surgical drain 225 is in the collapsed state. However, the decreased diameter of the distal portion of the surgical drain, which includes the portion of the surgical drain which traverses the skin and subcutaneous tissues 210, prevents ingress of air into the surgical drain during withdrawal, and also allows the distal portion of the device to be withdrawn with minimal pain and discomfort. Also shown in this figure is valve 205 for inflation and deflation of a diameter-varying element such as a balloon, and syringe 215.

Diameter-Varying Elements

As reviewed above, surgical drains of the invention may include a diameter-varying element. The diameter-varying element can be constructed of any material suitable for use in the body that can be used in the devices and methods of the subject invention, e.g., draining a fluid from a body cavity. Diameter-varying elements may vary, where examples of diameter-varying elements include, but are not limited to: wires, balloons, central spines, etc. Examples of various diameter-varying elements are now reviewed in greater detail below.

Wires

In some embodiments, the diameter-varying element is a wire. The wire in this embodiment can be made of a variety of biocompatible polymeric materials or metallic materials that combine flexibility or malleability, high strength, and high fatigue resistance. For example, the diameter-varying element can be formed using materials including, but not limited to: metals including stainless steel, titanium, alloys including a nickel-titanium alloy, a nickel-cobalt alloy, another cobalt alloy, tantalum, shape-memory materials, polymers, elastomers, polymer or elastomer blends and copolymers, elastic or superelastic materials, and combinations and mixtures thereof. The wires may also be coated, e.g., with a friction-reduction coating.

The cross-sectional configuration of the diameter-varying element in the form of a wire can be any suitable shape, such as round, oval, rectangular, square, etc. In some embodiments, the wire may have a flattened cross-sectional shape, such as a "ribbon" shape, and in some embodiments, the wire may be braided. The wire can also be formed into any suitable configuration, such as a straight line, a spiral, a double spiral, a triple spiral, etc., a coil, etc. In some embodiments, there can be more than one wire, such as two or more, three or more, etc. In some embodiments, the cross-sectional configuration of diameter-varying element in the form of a wire can change in cross-sectional configuration by a mechanical change, as disclosed above. For example, one or more wires in the wall of an elongated structure can be mechanically shortened such that the wires define a larger cross-sectional area by "bowing". The elongated structure can be held in the larger diameter configuration while in a body cavity by using a clip, for example, to hold the wires in the larger diameter configuration. In another example, a group of wires can be "wound" or "unwound" such that the wires change in cross-sectional configuration, e.g., from a tight spiral in the "wound" configuration, to a looser spiral in the "unwound" configuration. The lumen defined by the wires in the "wound" configuration can also have a smaller diameter than the lumen defined by the wires in the "unwound" configuration. In some embodiments, the alteration or change in a diameter-varying element can be controlled by remote means, such as with a radiofrequency or other electromagnetic signal, magnetic induction, etc. or automatic means, such as with a processor, etc.

In some embodiments the entire wire has the same configuration, and in other embodiments, at least a portion of the wire may have a different configuration, e.g., a spiral configuration in one segment of the wire, and a linear configuration in another segment of the wire. In some embodiments, the entire wire has the same diameter. In other embodiments, at least a portion of the wire has a different diameter from the remainder of the wire, e.g., a smaller diameter than the remainder of the wire. In some embodiments, where the surgical drain has a branched configuration, discussed further below, the wire can also have a branched configuration. The diameter and length of the wire will depend on the size and configuration of the surgical drain.

In some embodiments, the wire is "preformed". By "preformed" is meant that the wire is constructed of a material, such as a shape memory material, which allows the wire to have a preferred configuration. Suitable material for securing members can include shape memory materials, which are materials that have a temperature induced phase change, e.g., a material that if deformed when cool, returns to its "undeformed", or original, shape when warmed. Suitable material includes but is not limited to metals such as a nickel-titanium (NiTi) alloy (e.g., nitinol), a nickel-cobalt alloy, another cobalt alloy, alloys of CuZnAl, a thermoset plastic, stainless steel, a suitable biocompatible shape-memory material, a suitable biocompatible superelastic material, combinations thereof, and any suitable biocompatible shape memory alloy. In some embodiments, both the wire and the tubing can be preformed, e.g., both the wire and the tubing can be preformed into a spiral configuration.

FIGS. 3A and 3B show an embodiment of a surgical drain in which the diameter-varying element is a wire. FIG. 3A illustrates surgical drain 300 with a wire 310 in a straight configuration, which has been placed inside tubing 320. In FIG. 3B, the wire has been "preformed" into a spiral configuration, such that the tubing 320, which is supported by the wire, also forms a spiral configuration. Because the wire has been preformed into a spiral configuration, this facilitates the deformation of the small diameter tubing 320 into a functioning cylindrical drain 305 with a lumen whose diameter is much larger than either the wire or the small diameter tubing. When the surgical drain with this configuration is placed into a body cavity, the surrounding tissues complete the "wall" around the cylindrical drain. The application of suction or gravity drainage 340 to the proximal end of the drain which is external to the body results in the removal of air, liquid, solid or semi-solid material from the desired body cavity or space.

The embodiment of the surgical drain as shown in FIGS. 3A and 3B illustrates how the initial small diameter drain in FIG. 3A is transformed into the much larger diameter functioning surgical drain depicted in FIG. 3B by the insertion of a preformed wire. Although FIG. 3B is shown as a continuous wire, this embodiment could also include two preformed wires 310 coiled into a spiral configuration to deform two tubes 320 into a cylinder with a plurality of fenestrations 330. In another embodiment, the same functional result, e.g., a cylindrical drain with a much larger diameter with multiple fenestrations as shown in FIG. 3B, is constructed of preformed small diameter tubing. In this embodiment, small diameter tubing is used, where the tubing is formed of a material whose preformed shape forms a large functioning diameter tube or drain. In this embodiment, the diameter-varying element, e.g., a straightening wire, is inserted to reduce the diameter of the overall functioning cylindrical drain to the smaller diameter tubing at the time of insertion or withdrawal when the smaller diameter is desired.

Figure 4:
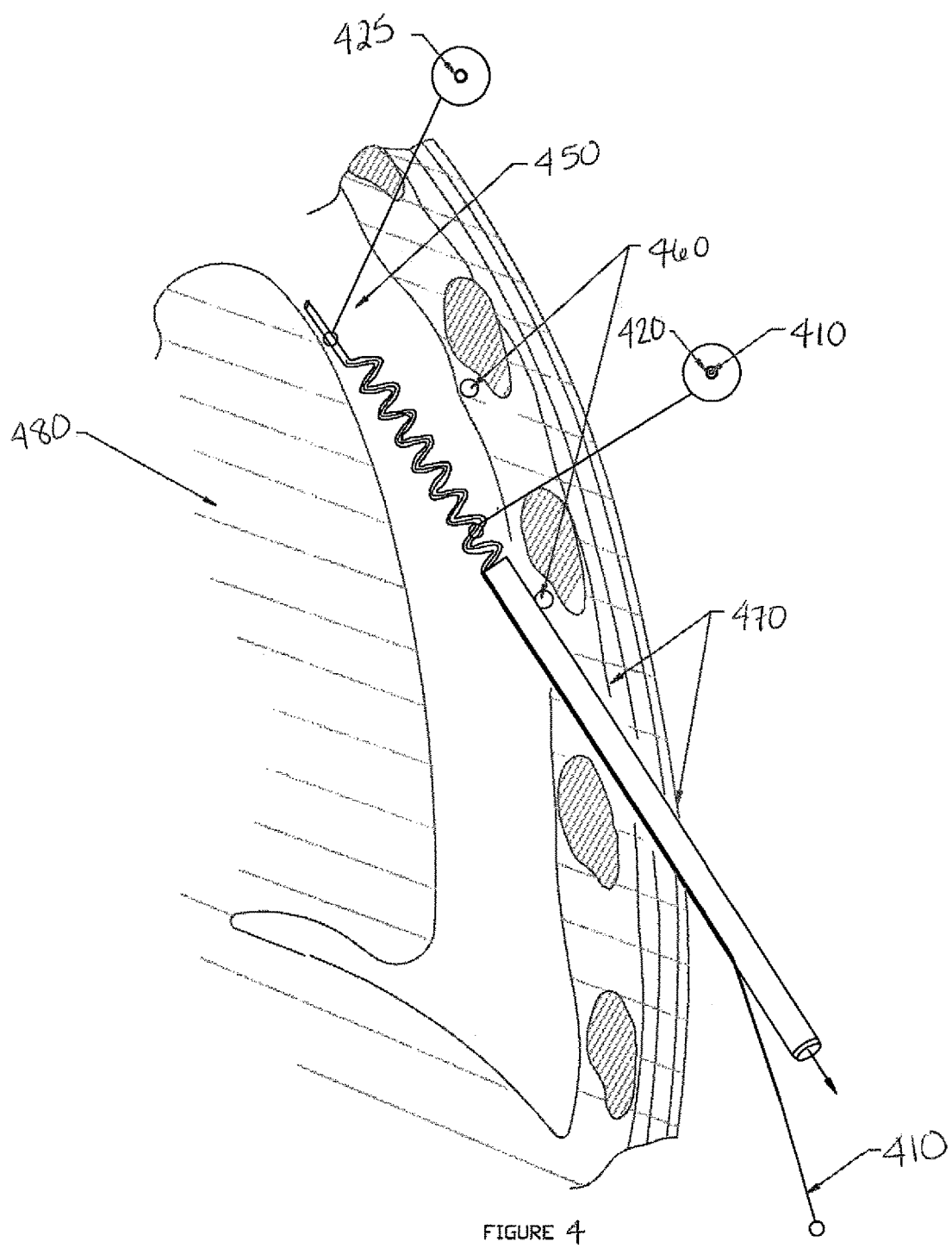
FIG. 4 provides a view of another embodiment of a surgical drain with a diameter-varying element in the form of a wire, according to an embodiment of the invention.

FIG. 4 is another embodiment of a surgical drain where the diameter-varying element is a preformed wire 410 inserted into tubing 420 thereby creating a cylinder draining the pleural cavity 450. As depicted, the wire 410 is partially withdrawn from the tubing (shown as element 425) which leaves the distal portion of the surgical drain formed by the spiral tubing unsupported by the wire 420. Removal of preformed wire 410 therefore results in the straightening of tubing 420, such that the surgical drain formed by the tubing alone now has a much smaller diameter, shown as straightened tubing 425. When removal of wire 410 is complete, the smaller diameter surgical drain can be removed from around lung 480 with significantly less pain detected by nerve endings in the pleural cavity 450, the intercostal nerve bundles 460 and the skin and subcutaneous tissues 470.

Figures 5, 5A, 5B:
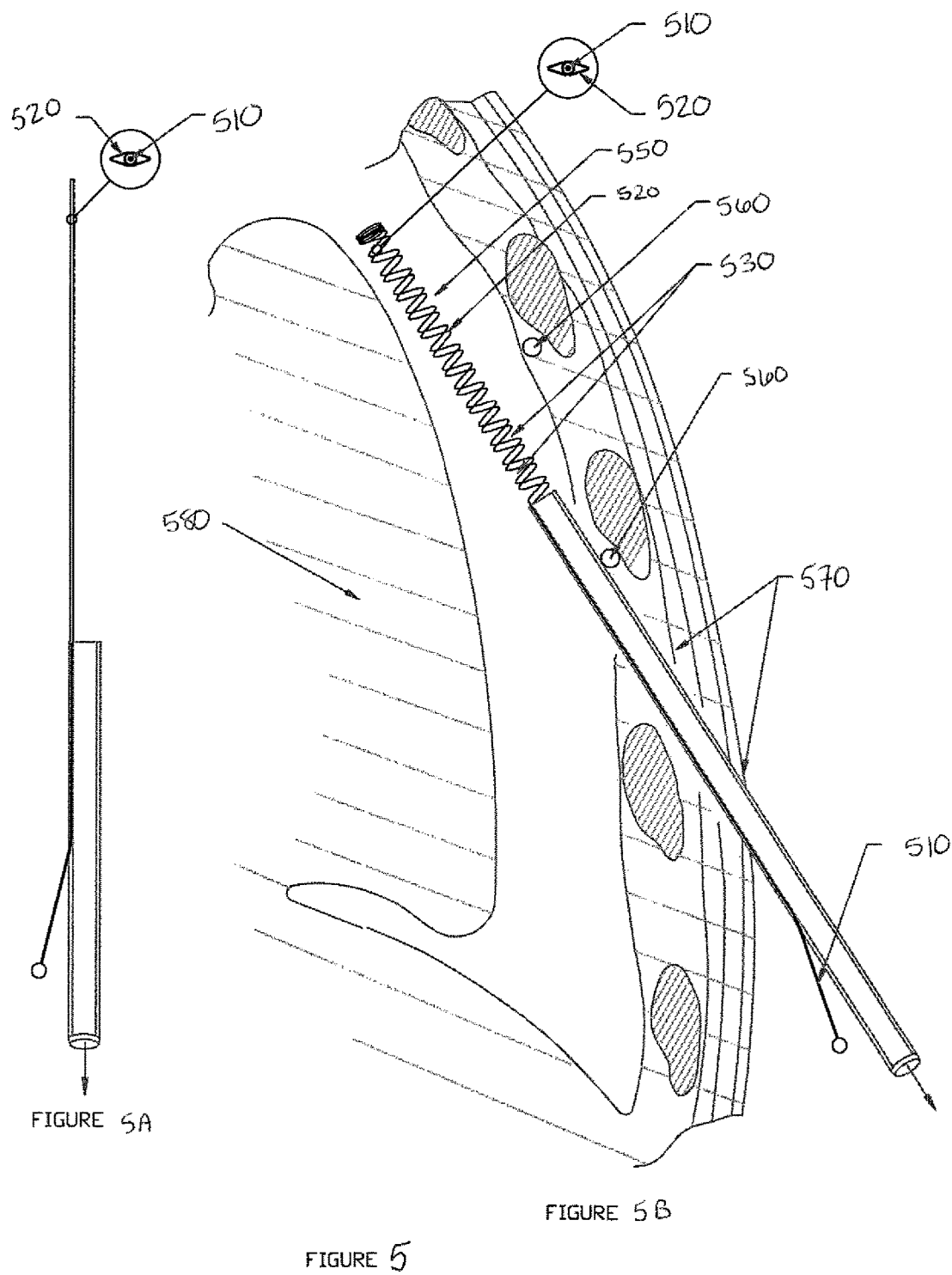
FIGS. 5A and 5B provide a view of an embodiment of a surgical drain with a diameter-varying element in the form of a wire, according to an embodiment of the invention.

The surgical drain embodiment in FIG. 5A is similar to the surgical drain shown in FIG. 4, except that in this embodiment, the small diameter tubing 520 has flanges, which increase the width of the tubing creating the cylindrical space of the surgical drain. In FIG. 5B, the embodiment of two preformed wires 510 inside two flanged tubes 520 is shown as a functioning surgical drain. In this embodiment, the cylindrical shape of the surgical drain with fenestrations 530 is created by the preformed wire 510 inside small diameter flanged tubing 520. The lumen formed by the tubing and wire can be used to remove air, body fluids, blood or clots. etc. from pleural space 550.

Balloons

In some embodiments, the diameter-varying element is a balloon. The balloon in this embodiment can be made of a variety of biocompatible polymeric materials or metallic materials that combine flexibility, high strength, and expandability. For example, the balloon can be formed using materials including, but not limited to: silicon, latex, polyurethane, polyimide or any other expandable and elastomeric material, and combinations or mixtures thereof.

The balloons can be filled with any material suitable for expanding the balloons, including but not limited to liquids, gasses, air, foam, including self-inflating foam material such as foamed polyurethane, or similar material. A self-inflating foam type material that can be used with the surgical drains of the subject invention can have a plurality of interconnected air pockets, such that a balloon can be deflated by using a syringe or other similar device to withdraw air out of the self-inflating foam.

The cross-sectional configuration of the diameter-varying element in the form of a balloon can be any suitable shape, such as spiral, coiled, linear, round, oval, rectangular, square, etc. In some embodiments, a plurality of balloons can be in the cross-sectional shape of "spokes on a wheel", for example, in which one or more balloons extend along the length of the elongated structure, and then extend out in a direction perpendicular to the long axis of the elongated structure. In some embodiments, one or more balloons can extend from the wall of the elongated structure at an angle, such as 25 degrees, 45 degrees, 65 degrees, etc. In some embodiments, the balloon may have a flattened cross-sectional shape, such as a "ribbon" shape. In other embodiments, the balloon may be a combination of shapes, such as for example, a balloon can have a spiral portion and a linear portion. The dimensions of a balloon may vary depending on the location of the balloon, the number of balloons in a particular surgical drain, and the size of the surgical drain. In some embodiments, the entire balloon has the same diameter. In other embodiments, at least a portion of the balloon has a different diameter, e.g., a smaller diameter. In some embodiments, at least a portion of the balloon may have both a different configuration and a different diameter, e.g., a portion of the balloon may have a smaller diameter and a spiral configuration, and the portion of the balloon may have a larger diameter and a linear configuration. In some embodiments, where the surgical drain has a branched configuration, discussed further below, the balloon can also have a branched configuration. The diameter and length of the balloon will depend on the size and configuration of the surgical drain. In some embodiments, there can be more than one balloon, such as one or more, or two or more, or three or more, etc.

In some embodiments, the cross-sectional configuration of the diameter-varying element in the form of a balloon can change in cross-sectional configuration by a mechanical change, such as winding, unwinding, twisting, untwisting, shortening or lengthening, etc. as disclosed above. In some embodiments, devices such as a slide, or a lock, a clip, etc., can be used to hold one or more balloons in a particular configuration, or can be used to seal a valve or syringe in order to maintain the balloons in an altered configuration. In some embodiments, the alteration or change in a diameter-varying element can be controlled by remote means, such as with a radiofrequency or other electromagnetic signal, magnetic induction, etc. or automatic means, such as with a processor, etc.

Figure 6:
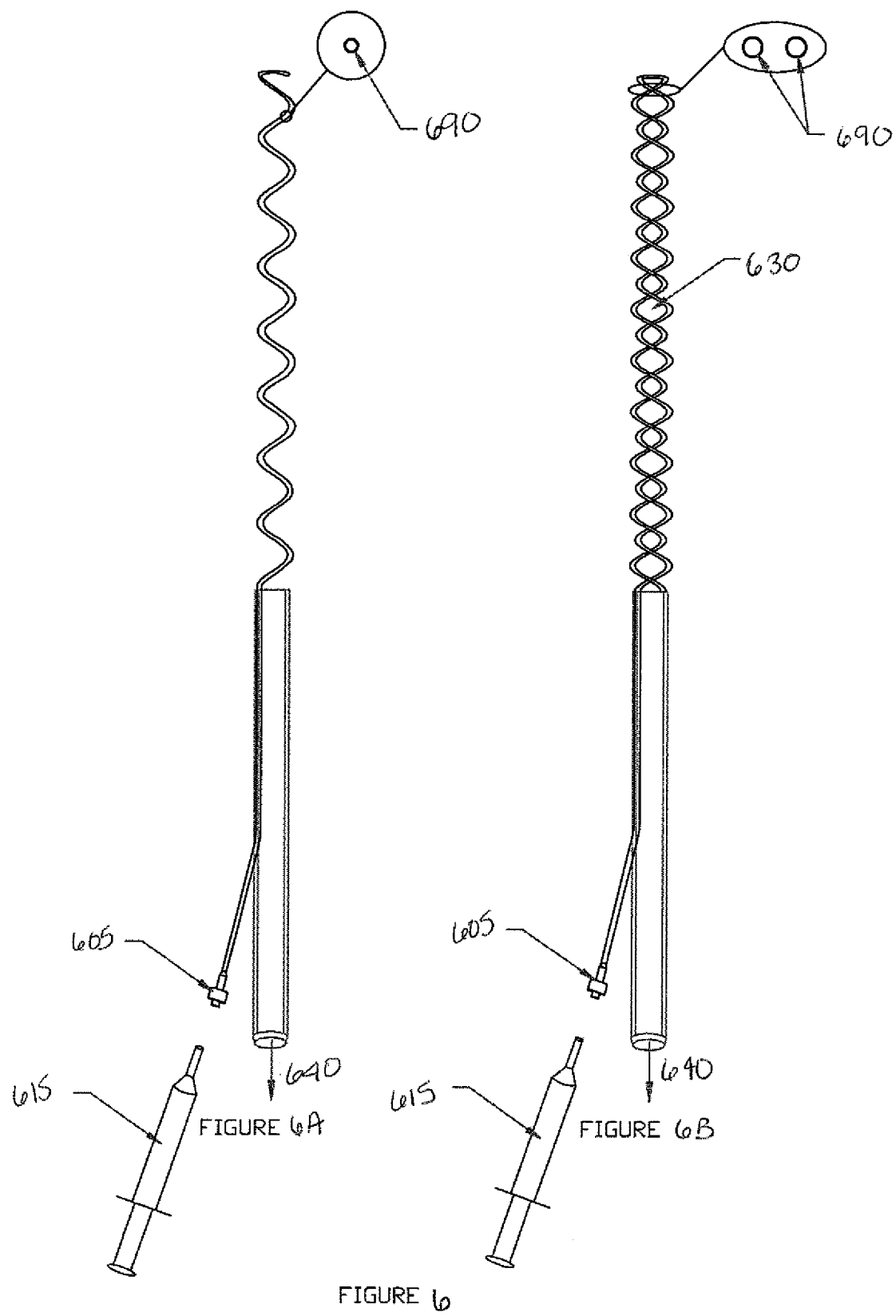
FIGS. 6A and 6B provide views of a surgical drain with a diameter-varying element in the form of a balloon, in accordance with an embodiment of the invention.

An embodiment of a surgical drain where the diameter-varying element is a balloon is depicted in FIGS. 6A and 6B. In this embodiment, the increased diameter of the surgical drain is created by insufflation of air into a coiled balloon 690. The air is insufflated through a one-way valve 605 with a syringe 615. Other fluids such as a liquid (e.g., saline), other gas, or a foam can also be used to inflate the balloons. FIG. 6A illustrates a single balloon in a spiral configuration. FIG. 6B shows dual balloons in a spiral configuration arranged in opposing coils, which creates fenestrations 630 allowing the application of suction 640 to the drain. Although two balloons are shown in FIG. 6B, embodiments of the invention include use of more than two balloons, such as three or more, or four or more, etc. In addition, embodiments can include a combination of diameter-varying elements, e.g., balloons, wires, etc.

Figure 7:
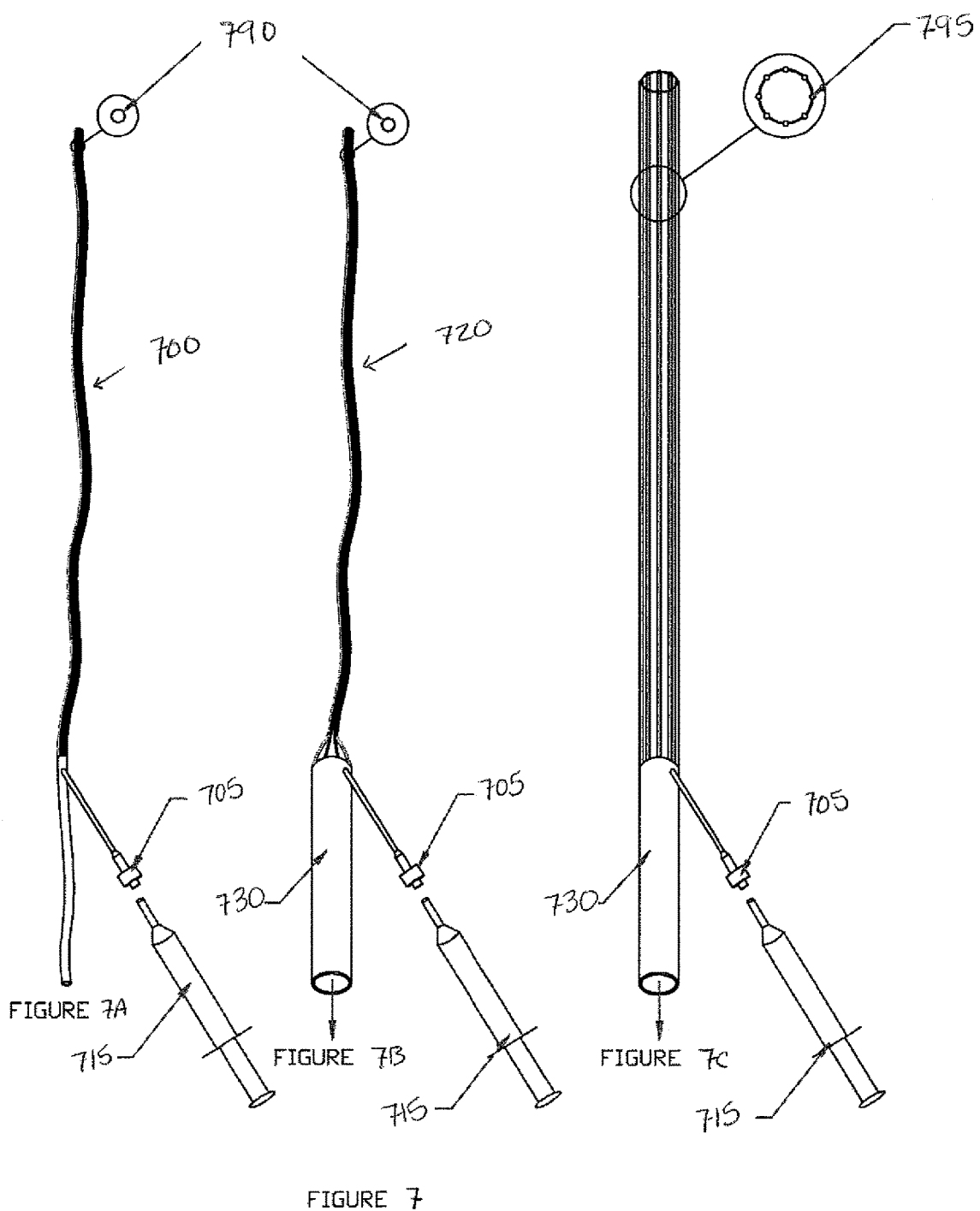
FIGS. 7A to 7C provide additional views of surgical drains with diameter-varying elements in the form of one or more balloons, according to an embodiment of the invention.

FIGS. 7A-7C depict another embodiment of a surgical drain where the diameter-varying element is a plurality of balloons 790, which can be insufflated with air through a one-way valve 705 from syringe 715. FIG. 7A depicts surgical drain 700 where the diameter has been decreased throughout the entire length of the surgical drain. In this embodiment, surgical drain 700 includes a diameter-varying element (e.g., one or more balloons) along the entire length of the surgical drain, where the balloons are integrated into the wall of the elongated structure of the drain. FIG. 7B shows another embodiment of surgical drain 720. In this embodiment, the diameter of the distal portion of the surgical drain has been reduced, while the proximal portion 730 is constructed of a solid material that maintains its diameter. In other words, this portion of the surgical drain does not contain a diameter-varying element. The proximal portion 730 with a fixed larger diameter facilitates connection to other devices, for example, a drainage apparatus, as discussed further below.

In FIG. 7C, the diameter-varying element in the form of a plurality of balloons 790 has been inflated with a fluid (e.g., foam, air, liquid) through one-way valve 705 from syringe 715. In this embodiment, inflation of the balloons results in a significant increase in the diameter of the surgical drain. The balloons in this embodiment are located in the wall of the surgical drain (i.e., integrated into the wall of the elongated structure), such that a ring of eight balloons, shown as element 795, are connected to form the wall of the elongated structure forming the surgical drain.

A cross-sectional view of the surgical drain as shown in FIG. 7C is further illustrated in FIG. 8A. In this embodiment, the increased diameter of the drain while the drain is functioning is supported by a plurality of balloons 890 filled with self-inflating foam 835. FIG. 8B shows a cutaway view of the same embodiment. Connecting hoop strengthening elements 845 between balloons 890 create fenestrations 830. The presence of fenestrations allows for egress of drained material while the drain in placed in a body cavity. When the drainage function is no longer desired, the air or other gas contained in the balloons filled with self-inflating foam is aspirated via a syringe and one-way valve. The diameter of the drain is thus greatly reduced and the drain can be withdrawn with a significant decrease in the pain experienced by the patient.

Figure 9:
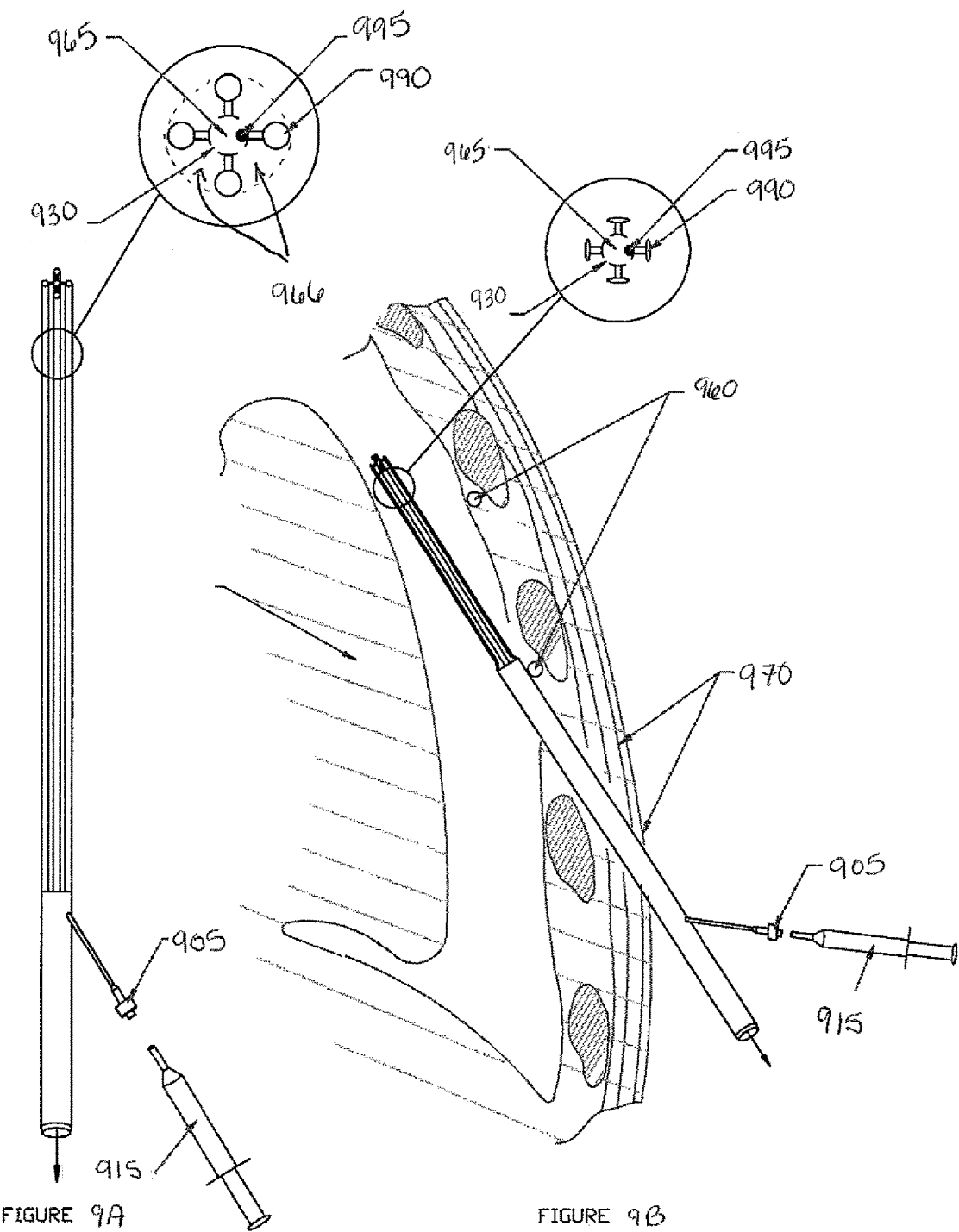
FIGS. 9A and 9B provide a view of an embodiment of a surgical drain with a diameter-varying element is in the core of the elongated structure, according to an embodiment of the invention.

FIGS. 9A and 9B depict an embodiment of the invention where the elongated structure consists of a "wall" in a cross-shaped configuration, where the diameter-varying element (e.g., balloons, shown as element 990) are in the wall of the elongated structure, as shown in FIG. 9A. In this embodiment, there is a central drainage lumen, shown as element 965, which further has fenestrations 930. Also shown is a wire 995 present in the central drainage lumen, an embodiment which is discussed further below. The central lumen may or may not have a wire, e.g., a guidewire. In this embodiment, the "wall" also defines four peripheral lumens, as discussed above, shown as element 966 inside the dotted line. The walls of the peripheral lumens are partially formed by adjacent "arms" of the cross, and partially formed by the surrounding body tissue when the elongated structure is placed in a body cavity. Therefore, in this embodiment there are five drainage lumens. FIG. 9B depicts the same embodiment, with the difference being that in FIG. 9B the diameter-varying element (e.g., the balloons in the wall of the elongated structure 990) has been deflated by aspirating air via a syringe 915 connected through one-way valve 905. The deflated elongated structure is withdrawn, which results in decreased pain for the patient transmitted via the intercostal nerve bundles 960 and skin and subcutaneous tissues 970.

Central Spline

In some embodiments, the diameter-varying element is a central spline. A central spline is an elongated flexible member that can be inserted or removed from the core portion of a surgical drain, thereby providing a flexible, internal soft support. The central spline in this embodiment can be made of a variety of biocompatible polymeric materials or metallic materials including, but not limited to: silicone, polymers, thermoplastic elastomers, plastic, rubber, biodegradable material, metals, alloys, any other suitable material, and combinations or mixtures thereof.

The cross-sectional configuration of the diameter-varying element in the form of a central spline can be any suitable shape, such as a cross, round, oval, rectangular, square, etc. In some embodiments, the central spline can have one or more additional diameter-varying elements, such as a wire, or one or more balloons. The additional diameter-varying element, such as a balloon, can be in the center of the central spline, or around the edges of the central spline. The diameter-varying element, when present, may or may not be integrated with the central spline. By integrated is meant that the diameter-varying element cannot be separated from the central spline without irreparably altering the central spline. Examples of non-integrated configurations are where the diameter-varying element is a wire which can be separated from the central spline without comprising the central spline. In some embodiments, the central spline itself can therefore change in diameter. For example, one or more balloons integrated into a central spline can be deflated before the central spline is removed. In other embodiments, the central spline may be a combination of shapes, such as for example, a central spline which has the cross-sectional configuration of a cross in one portion of the spline, and a round configuration in another portion of the spline. In some embodiments the entire spline has the same shape, and in other embodiments, at least a portion of the spline may have a different shape.

In some embodiments, the entire spline has the same diameter. In other embodiments, at least a portion of the spline has a different diameter than the remainder of the spline, e.g., a smaller diameter than the remainder of the spline. In some embodiments, at least a portion of the spline may have both a different configuration and a different diameter, e.g., a portion of the spline may have a cross-sectional configuration in a cross, with a larger diameter, and a potion of the spline may have a round cross-sectional configuration, with a smaller diameter.

In some embodiments, the cross-sectional configuration of a central spline can change in cross-sectional configuration by a mechanical change, such as winding, unwinding, twisting, untwisting, shortening or lengthening of the central spline, etc. In some embodiments, devices such as a slide, or a lock, a clip, etc., can be used to hold a central spline in a particular configuration. For example, a central spline can be "wound" or "unwound" such that the central spline changes in cross-sectional configuration, e.g., from a tight spiral in the "wound" configuration, to a looser spiral in the "unwound" configuration. A central spline in the "wound" configuration can also have a smaller diameter than a central spline in the "unwound" configuration. In some embodiments, the central spline can include one or more flanges, wings, paddles, appendages, etc., which can be deployed in the larger diameter configuration and retracted or overlapped in the smaller diameter configuration. In some embodiments, the alteration or change in a diameter-varying element can be controlled by remote means, such as with a radiofrequency or other electromagnetic signal, magnetic induction, etc. or automatic means, such as with a processor, etc.

In some embodiments, when the diameter-varying element is a central spline, the central spline may further be attached to the proximal or the distal end of the surgical drain, such that it can be withdrawn with the surgical drain, or it can be inverted and withdrawn, depending on the point of the attachment. In these embodiments, the surgical drain would be made of material sufficiently flexible to invert. In some embodiments, where the surgical drain has a branched configuration, discussed further below, the spline can have a branched configuration. The diameter and length of the spline will depend on the size and configuration of the surgical drain.

Figure 10:
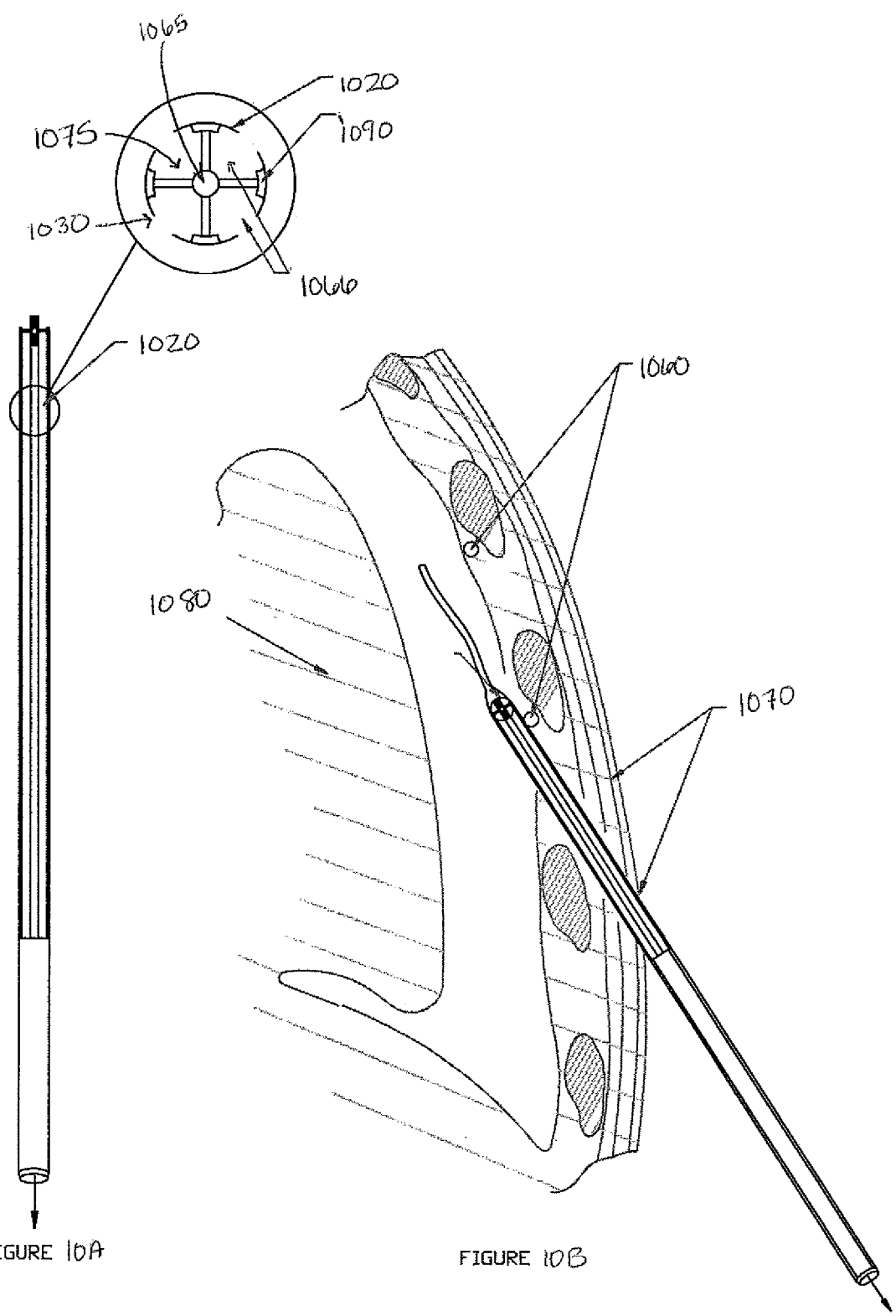
FIGS. 10A and 10B provide additional views of surgical drains wherein the diameter-varying element is in the core of the elongated structure.

FIGS. 10A and B show an embodiment of the invention in which the diameter-varying element is a central spline. In this embodiment, a surgical drain 1020 perforated with fenestrations 1030 is supported by a central spline 1075. Central spline 1075 is an internal soft support configured to be placed in the lumen of an elongated structure, such as surgical drain 1020. The cross-sectional shape of central spline 1075 in FIG. 10A is in the form of a cross. The central spline can in some embodiments include balloons, such as the four balloons 1090 shown in the central spline 1075, which can be inflated during the period the drain is functioning in order to provide a larger diameter. In this embodiment, the central spline has a central drainage lumen, shown as element 1065, which may or may not have a wire present in the lumen, e.g., a guidewire. In this embodiment, the central spline divides the lumen of the elongated structure into sections, such that there are four peripheral lumens (element 1066) created by the central spline, in addition to the central lumen 1065.

FIG. 10B depicts the withdrawal of the diameter-varying element or central spline when the larger diameter is no longer necessary. The internal supporting structure provided by the central spline is simply withdrawn if constructed of soft solid material. In this embodiment, prior to removal of the drain, the balloons 1090 in the central spline 1075 can also be deflated. The surgical drain 1020 is then withdrawn in its collapsed state. In some embodiments, when the diameter-varying element is a central spline, the central spline may further be attached to the proximal end or the distal end of the surgical drain, such that it can be withdrawn with the surgical drain, or it can be inverted and withdrawn, depending on the point of the attachment.

Branches

In some embodiments, the surgical drain of the subject invention may further comprise branches. By "branches" or "limbs" is meant one or more extensions, or limbs, of the main portion of the surgical drain that can increase drainage capacity of a surgical drain of the subject invention. For example, in draining a body cavity in the chest, one branch or limb can be placed in the upper portion of the chest, and another branch can be placed at the base of the chest. A surgical drain can therefore have two or more branches, or three or more branches, or four or more branches, etc. The branches may, in some embodiments, have a diameter that is smaller than the diameter of the proximal portion of the surgical drain.

In some embodiments, when the diameter-varying element employed is a wire, the limbs of a surgical drain may be positioned either by using wire that has been pre-formed into a desired shape, or by using malleable wire. In addition, any of the embodiments of wires as disclosed above can be used in the creation and placement of branches of a surgical drain. In other embodiments, any suitable pre-formed or malleable polymer, plastic, or similar material can be used to provide placement accuracy for the branches of the surgical drain. As discussed above, in some embodiments, the diameter-varying element employed in a surgical drain of the subject invention can be a balloon, or a central spline.

Figure 11:
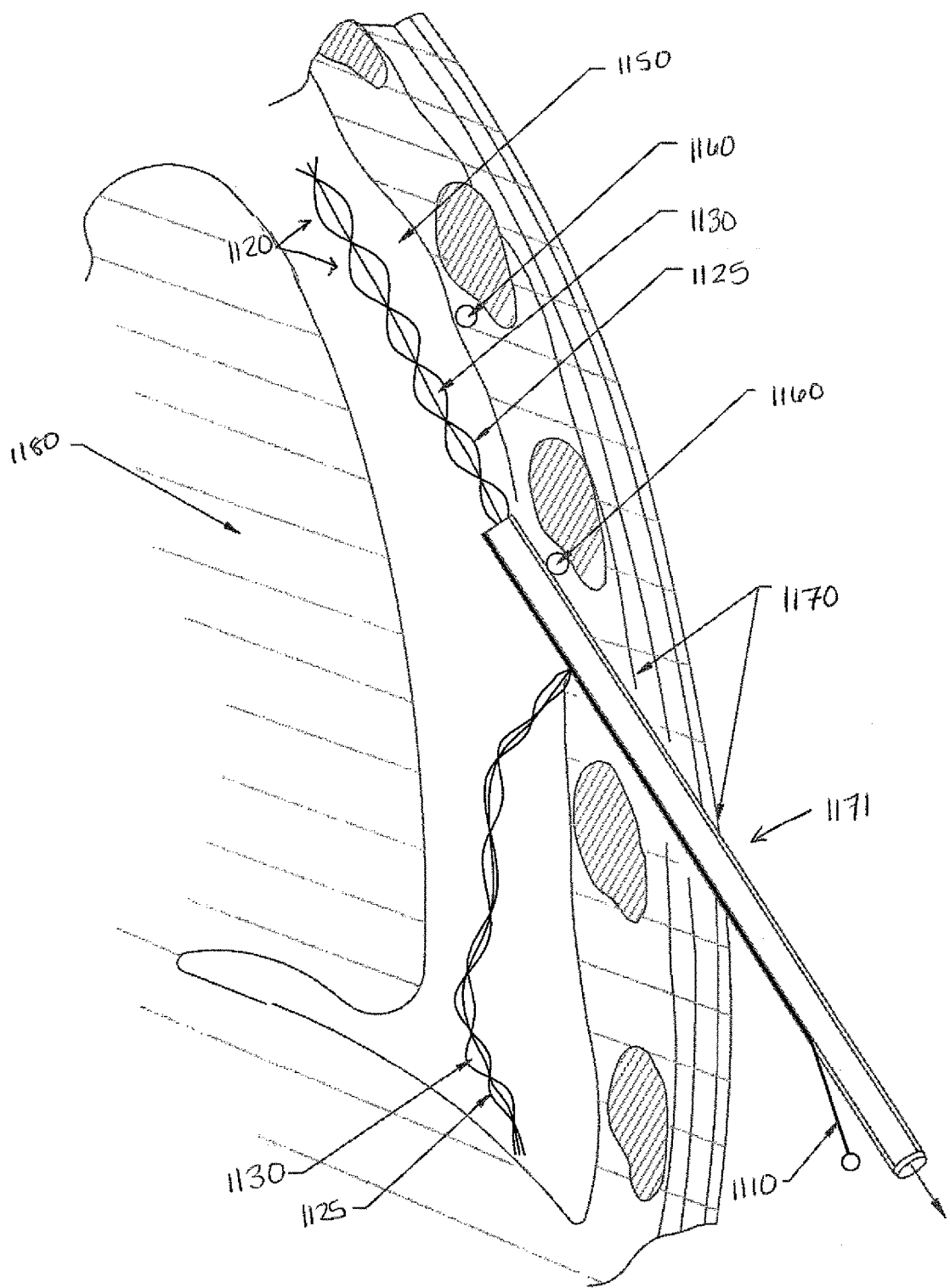
FIG. 11 provides a view of an embodiment of the surgical drain with branches, according to an embodiment of the invention.

FIG. 11 illustrates an embodiment of the surgical drain in the chest cavity, showing that a plurality of diameter-varying elements in the form of multiple wires can be used to define additional branches of the surgical drain. The plurality of drainage limbs 1125 (in this example, two branches are shown) are in continuity with the proximal portion of the surgical drain which exits the body cavity and skin 1170. This embodiment is similar to the embodiment of the surgical drain as shown in FIGS. 3A-4, in that each branch of the drain is formed by tubing 1120 through which preformed wires 1110 are inserted. The tubes 1120 are formed into a branch which has a larger effective diameter for the drainage lumen than a single tube alone would create. The branch 1125 has a plurality of fenestrations 1130. The wires can be malleable such that the branches of the surgical drain can be positioned in specific locations, in order to achieve wide drainage. For example, as shown in FIG. 11, one branch 1125 extends superiorly to evacuate air from the upper portion of the thoracic cavity, and the lower branch extends inferiorly to drain or evacuate body fluids, blood or clot from the lower portion of the thoracic cavity. However, in this embodiment, both branches can drain both fluid and air. When drainage is no longer desired, the collapsible nature of the branches allows for withdrawal of the reduced diameter(s) of the surgical drain through a single skin incision 1171. Also shown are the pleural cavity 1150, lung 1180, and the intercostal nerve bundles 1160.

Figure 12:
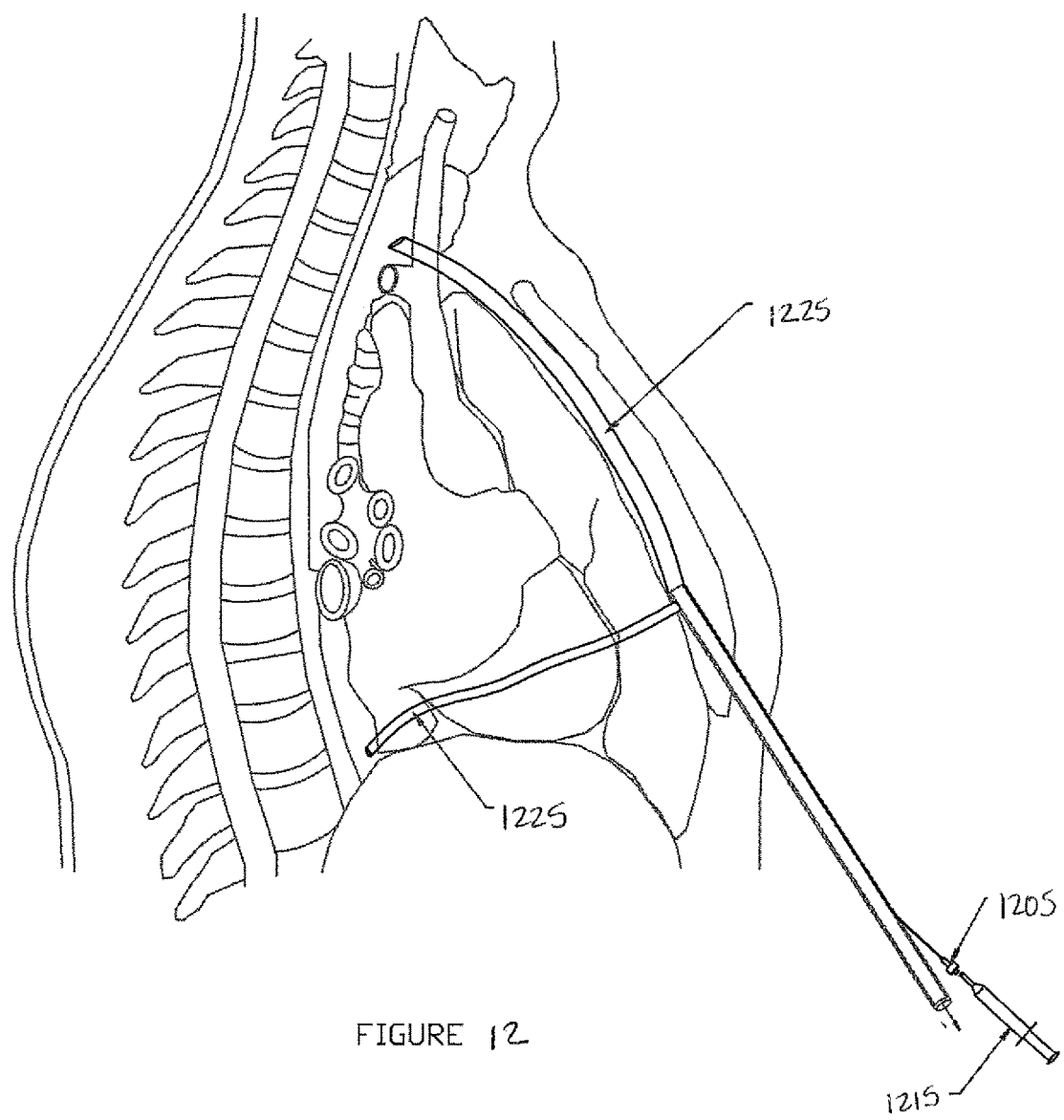
FIG. 12 provides a view of another embodiment of a surgical drain with branches, showing a lateral view of the thoracic cavity, according to an embodiment of the invention.
Figure 13:
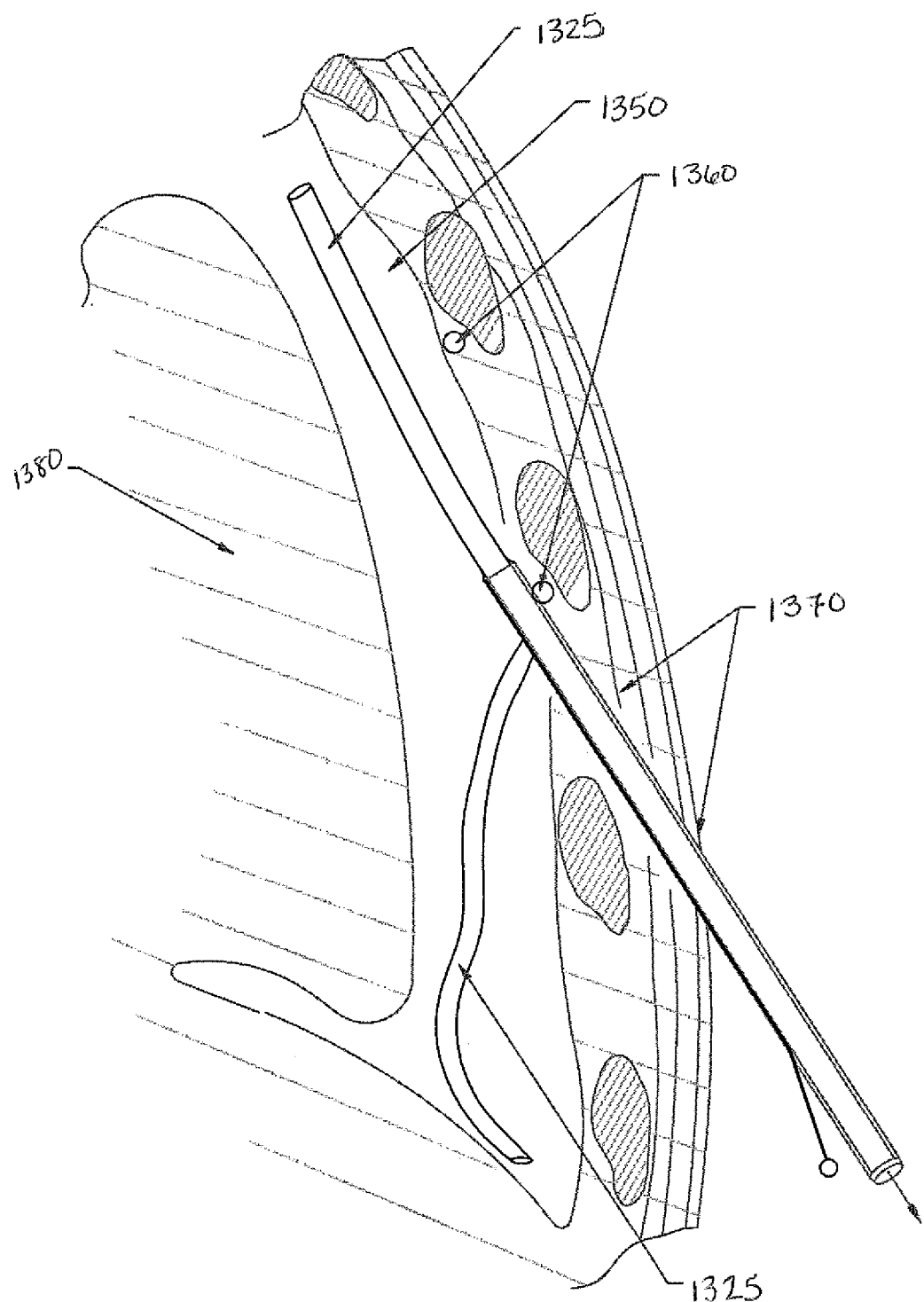
FIG. 13 provides a view of the embodiment of the surgical drain as in FIG. 12, showing an anterior to posterior view of the thoracic cavity, according to an embodiment of the invention.

FIG. 12 illustrates another embodiment of a surgical drain with branches placed in the chest cavity, shown in a lateral view. In this embodiment, the surgical drain includes two drainage limbs 1225 within the pleural space, one placed superiorly, and one placed inferiorly. Also shown in this figure is valve 1205 for inflation and deflation of a diameter-varying element such as a balloon, and syringe 1215. A similar view is shown from the anterior posterior view in FIG. 13. The element of another diameter-varying element, such as a wire, which provides support to the surgical drain, can also allow malleability and steerability of the one or more branches 1325 of the surgical drain. However, prior to the time of withdrawal of the surgical drain, the limbs can be collapsed to minimize contact with the pain nerve endings. These nerves can be found in the pleural cavity 1350, at the intercostal nerve bundles 1360 and at the skin and subcutaneous tissues 1370. Further, the embodiment of the surgical drain of the subject invention can be withdrawn through a single skin incision, thus minimizing the number of skin and subcutaneous pain nerve endings exposed to the subject surgical drain while the drain is indwelling and during removal.

Figure 14:
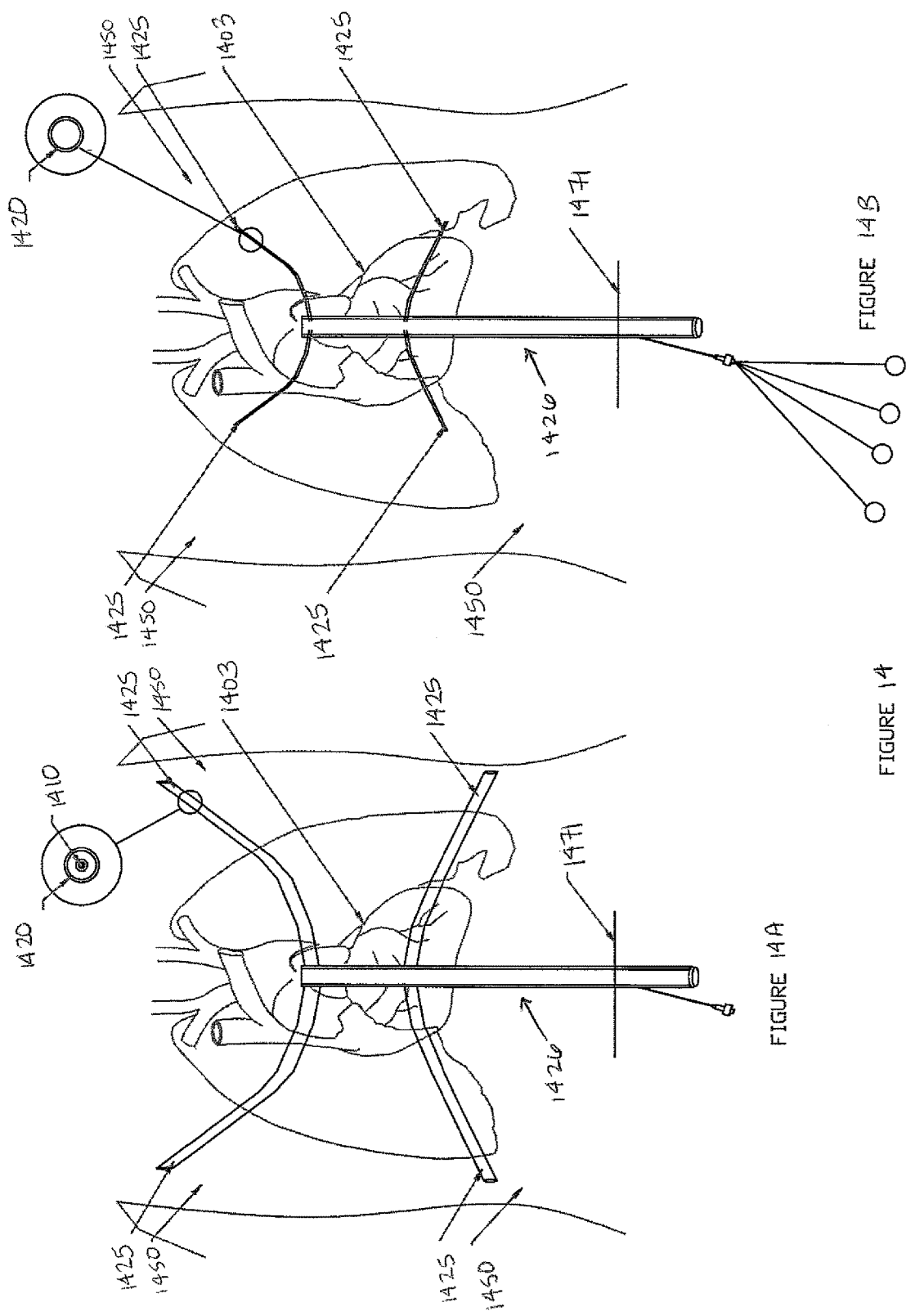
FIGS. 14A and 14B provide views of another embodiment of a surgical drain with branches, showing an anterior to posterior view of the thoracic cavity before and after removal of the diameter-varying element, according to an embodiment of the invention.

FIGS. 14A-B are schematic views in the anterior to posterior projection of the entire thoracic cavity showing the wide drainage achievable with subject surgical drain. A plurality of limbs 1425 can be used, and in this example four limbs are shown. These limbs of the surgical drain have been placed in order to optimize drainage of the pericardial space and mediastinum 1403 and pleural cavity 1450. In this view, the surgical drains are in their expanded state. In this embodiment, the diameter-varying element is shown as wire 1410 inside tubing 1420. This extensive drainage can be achieved via a drain that exits the skin 1471 in one location, because the surgical drain is collapsible. FIG. 14B is another schematic view in the same anterior to posterior projection of the entire thoracic cavity, with the branches 1425 depicted in the collapsed state, after removal of wire 1410, as the drain is readied for withdrawal via the single skin incision 1471. In another embodiment, the branched elongated structure as shown in FIG. 14B can also include collapse of the entire drain structure, i.e, both branches 1425 and the central proximal portion of the drain 1426 which traverses skin incision 1471.

Delivery Lumen

In some embodiments of the invention, the surgical drain includes, in addition to the lumen configured to drain a substance from a body cavity, an additional lumen in the wall of the elongated structure configured to deliver a substance into the body cavity. Substances that can be delivered into the body cavity through an additional lumen can include pharmaceutical agents such as antibiotics, anti-clotting agents, anesthetic agents, etc. Pharmaceutical agents can be administered while the drain is in place. For example, they can be administered continuously or intermittently for therapeutic treatment of infection, for example. In other embodiments, pharmaceutical agents can be administered in a single dose, for example, if it is desired to administer an anesthetic agent along the tract of the drain prior to withdrawal of the drain. In some embodiments, there can be more than one lumen. The lumen configured for delivery of a therapeutic substance, such as a pharmaceutical agent, can have a valve on the end, and can be attached to a syringe for delivery of the agent. In some instances, such lumens are in fluid flow relationship with a source of the therapeutic agent, e.g., a fluid reservoir of the therapeutic agent. Such source may be positioned at any convenient location, such as the proximal end of the surgical drain.

Figure 15:
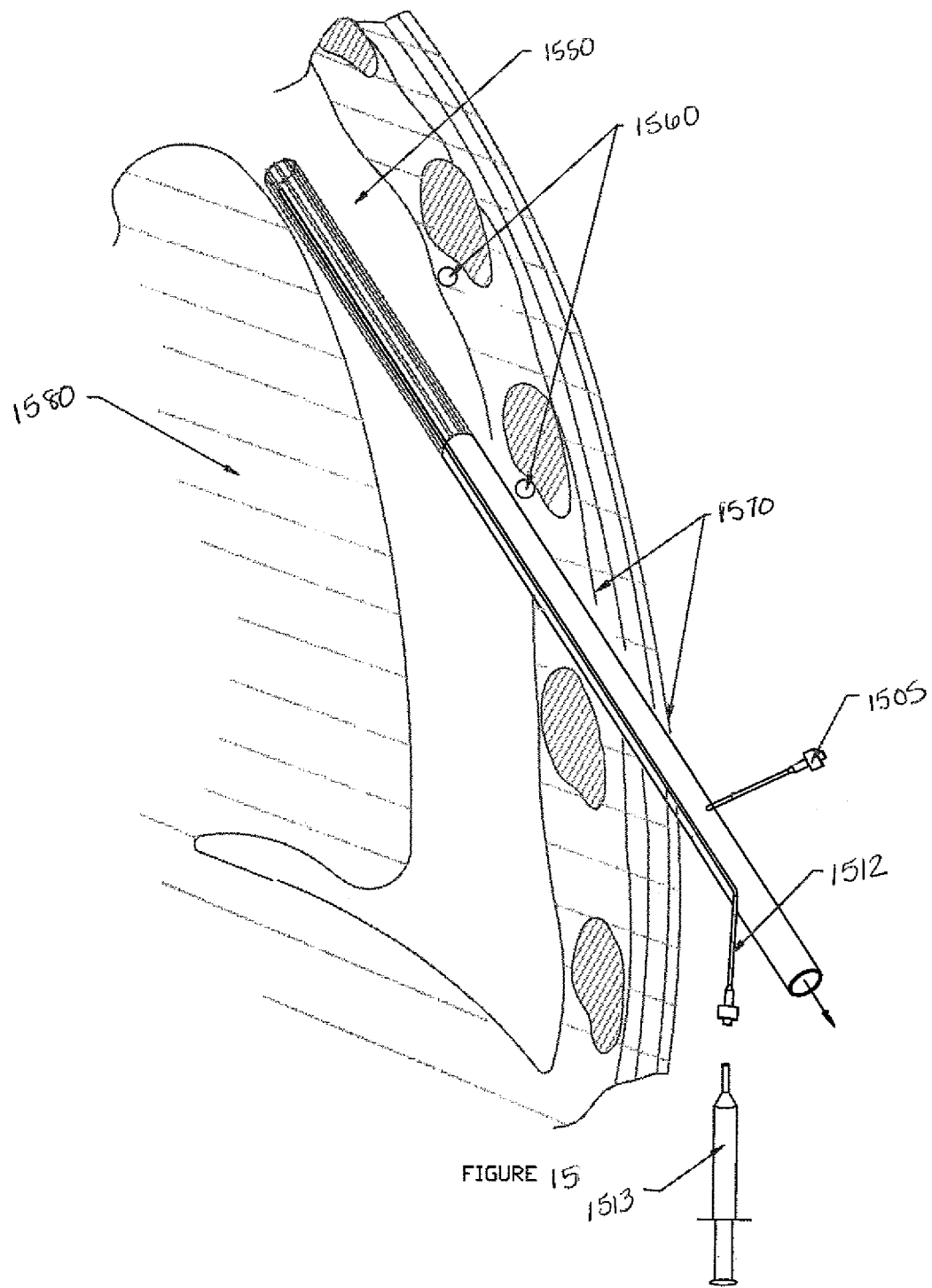
FIG. 15 provides a view of the proximal portion of the surgical drain, which exits the body cavity and is fixed to the skin, according to an embodiment of the invention.

FIG. 15 is a schematic of the invention showing the proximal portion of the drain, which exits the pleural cavity and is fixed to the skin 1570. This embodiment shows the incorporation of tubing 1512 into the device. The tubing 1512 may be present throughout the entire length of the device, or the tubing may be present only in a portion of the device, e.g., in the proximal third, or the proximal half of the surgical drain, etc. Medications to treat disease may be given via tubing 1512 and syringe 1513, which serves as the source of a therapeutic agent. As shown in the figure, syringe 1513 is positioned at the proximal end of the drain. In addition, medications to provide local anesthesia may be administered prior to removal of a surgical drain to decrease the pain associated with withdrawal of the device.

Coating

The surgical drain of the subject invention can also include a coating around a surface of the surgical drain. By "coating" is meant a substance that is applied to a surface of a surgical drain or sheath. In some embodiments, the coating may be a coating that reduces friction, such as a friction-reduction coating, or it may be a coating that contains a pharmaceutical agent, e.g. an agent that decreases the risk of blood clot formation, a coating that decreases the risk of infection, a coating that decreases pain, etc.

In some embodiments, the elongated structure may include a friction-reduction coating. Substances that may be used in a friction-reduction coating can include, but are not limited to: low friction polymers such as fluoro-ethylene co-polymer (FEP), other low friction coatings that include paralyne, silicone, Teflon® coating, etc. In some instances, the presence of a friction-reduction coating on the outside of a surgical drain decreases patient discomfort with removal of the drain. In instances, the presence of a friction-reduction coating on the inside surface of a surgical drain improves the function of the surgical drain, for example by decreasing the chances of a surgical drain becoming clogged by draining substances. A friction-reduction coating on the inside surface of a surgical drain could also the diameter of a surgical drain to be reduced while preserving the same capacity for drainage.

Methods of Using a Surgical Drain

Aspects of the invention further include methods of using a surgical drain in accordance with the invention, e.g., as described above, to drain a substance from a body cavity. The methods of using a surgical drain of the subject invention can include positioning a distal end of an elongated structure in a body cavity, draining a substance from the body cavity, decreasing the diameter of the distal end of the elongated structure prior to removal of the elongated structure, and then removing the distal end of the elongated structure from the body cavity.

The distal end of a surgical drain of the subject invention can be positioned in the body cavity during an open surgical procedure, during a minimally invasive procedure (e.g., with an endoscope), or can in some embodiments be inserted percutaneously. The methods of the subject invention can also include the use of imaging guidance, such as xray, fluoroscopy, CT, ultrasound, MRI, nuclear medicine, etc., as well as other methods of visualization such as fiberoptic visualization, or endoscopic visualization. Furthermore, the methods can include procedures performed in a medical setting such as a hospital, clinic, office, radiology or fluoroscopy suite, and can also include procedures performed anywhere medically necessary, e.g. a battlefield.

By "open surgical procedure" is meant a surgery which is performed through a surgical incision allowing access and visualization of the portion of the body of interest. In some embodiments, the distal end of the elongated structure can be placed into a body cavity during an open surgical procedure. A body cavity that is exposed during an open surgical procedure can be referred to as an "open body cavity".

By "minimally invasive surgical procedure" is meant a surgery which is performed through a surgical incision or body opening that is smaller than the incision required for an open surgical procedure. A minimally invasive surgical procedure generally includes the use of one or more endoscopic instruments for allowing access and visualization of the portion of the body of interest. By "endoscope" or "endoscopic instrument" is meant a thin tube-like instrument used to examine or enter the inside of the body of a subject, e.g., the thoracic cavity. An endoscope can have a light and a lens or camera for viewing the inside of the body, and can also have one or more tools that can be used with an endoscope, such as a tool that can be used to place a surgical drain, or place a sheath over a drain, etc. One or more openings, or "ports" can be created in one or more locations in the body, e.g., the intercostal spaces of the chest, depending on the procedure to be performed and the endocoscopic instruments to be used. One or more endoscopes or endoscopic instruments can be advanced through at least one of the endoscopic body openings. In some embodiments, the distal end of the elongated structure can be placed into a body cavity during a minimally invasive surgical procedure.

By "percutaneously" is meant insertion of a surgical drain through a skin incision or body opening that can be smaller than the incision required for an open surgical procedure or a minimally invasive procedure. The skin opening can be just large enough to allow the surgical drain to be inserted into the body cavity. In this embodiment, placement of a surgical drain can also be achieved by percutaneously creating an opening into a body cavity through a skin incision, and using implements such as a needle, trocar, cannula, introducer, sheath, dilator, or the like through the opening. Percutaneous placement can include non-guided techniques or guided techniques including but not limited to the use direct visualization, such as fiberoptic visualization, or endoscopic visualization, or imaging guidance as discussed above.

The step of draining a substance from the body cavity using the subject surgical drains can include allowing a body fluid, e.g., a liquid, air, blood, or other substance to drain from a natural or created body cavity. Draining a body cavity can be performed for as long as necessary for a therapeutic effect; e.g., until the body cavity ceases to drain, or until the supervising physician or other healthcare provider determines that the drain is no longer necessary. Drainage of a body cavity can occur over a period of minutes, hours, days, weeks, months or years, depending on the medical condition.

The devices of the subject invention can be used for insertion into any body cavity in need of draining, such as a thoracic body cavity, which includes a body cavity in the chest including a pleural body cavity or pericardial body cavity, an abdominal body cavity, a gastrointestinal body cavity, a pelvic body cavity, a genitourinary body cavity, a cavity in the brain or spinal cord, a cavity in an extremity such as an arm or leg, etc. Further, the body cavity can be an anatomical or "natural" body cavity, e.g., the pleural space, or peritoneal space, or it can be a surgically-created or disease-created body cavity, e.g., an abscess cavity. In some embodiments, the body cavity can be a cavity in a solid organ, (e.g., liver, bone, etc.) In some embodiments, the body cavity can be a hollow organ, or an organ with a lumen, such as a urethra, a ureter, a portion of the intestine, the esophagus, the trachea, or a bronchial tube. Further, the devices can be inserted through an orifice and/or through an incision in the skin.

The subject surgical drain, during use, is maintained in the larger diameter while present in the body cavity in order to provide the largest area for drainage of the substance from the body cavity. Prior to removal of the surgical drain, the diameter of the distal end of the surgical drain is decreased, which allows for easier removal of the surgical drain, and significantly decreases patient discomfort associated with the procedure.

As discussed above, the change in diameter of the distal end of the surgical drain is mediated by a diameter-varying element. The change in diameter may be mediated by a diameter-varying element in a number of different ways. For example, the diameter may be changed by introducing the diameter-varying element into the drain. Alternatively, the diameter-varying element may be changed by removing the diameter-varying element from the drain. These examples are not limiting, and embodiments of mediation of diameter change by a diameter-varying element are described further in greater detail below.

In some embodiments, decreasing the diameter of the elongated structure comprises inserting a diameter-varying element into the elongated structure before the elongated structure is removed from the body cavity. For example, in the case of a surgical drain made of a preformed tubing in a spiral configuration, the diameter-varying element can be a wire in a straight configuration that, when inserted into the tubing in the wall of the surgical drain, will straighten the spiral tubing, thereby decreasing the overall diameter of the surgical drain.

In some embodiments, decreasing the diameter of the elongated structure comprises removing a diameter-varying element from the elongated structure before the elongated structure is removed from the body cavity. For example, in the case of a surgical drain made of a preformed wire inside tubing, where the wire is in a spiral configuration, the diameter-varying element in this embodiment is the wire in a spiral configuration. The spiral configuration of the wire which deforms the tubing into a spiral configuration results in a larger diameter of the surgical drain while the surgical drain in present in the body cavity. Once the preformed wire in a spiral configuration is removed from the tubing, the tubing will straighten, thereby decreasing the overall diameter of the surgical drain. In another example, a surgical drain can have a central spline in the core portion of the surgical drain, which creates a larger diameter while the surgical drain is present in the body cavity. Once the central spline is removed from the core portion of the surgical drain, the unsupported wall of the surgical drain will decrease in diameter.

In some embodiments, the diameter-varying element is present in the wall portion or the core portion of a surgical drain and is altered before the surgical drain is removed from the body cavity. For example, in the case of a surgical drain in which the diameter-varying element includes one or more balloons filled with foam in the wall portion of the surgical drain, the filled balloons in the wall result in an expanded wall portion of the surgical drain, and therefore a larger diameter of the drain while the surgical drain in present in the body cavity. Once the foam is removed from the balloons, the surgical drain will decrease in size, thereby decreasing the overall diameter of the surgical drain.

In some embodiments, therefore, the diameter of the elongated structure is decreased before positioning the elongated structure in a body cavity, and increased after being positioned in a body cavity. In some embodiments, the diameter of the elongated structure is decreased before withdrawing the elongated structure from the body cavity. In some embodiments, the diameter of the elongated structure can be changed from a larger diameter to a smaller diameter and back again while the distal end of the elongated structure is positioned in a body cavity. In other embodiments, the diameter of the elongated structure can be changed from a large diameter to an even larger diameter to increase drainage surface area while the distal end of the elongated structure is positioned in a body cavity. In some embodiments, the change in diameter can be performed more than once, for example, such as two or more times, or three or more times, etc., while the elongated structure is positioned in a body cavity. Changes in diameter can be performed to improve drainage of thicker material from the elongated structure, e.g., removal of clots, debris. For example, a diameter-varying element can be inserted, or removed, or altered as disclosed above while the elongated structure is indwelling in the body. In some embodiments, change in diameter can be by mechanical means, as disclosed above. In some embodiments the change in diameter mediated by the diameter-varying element can be controlled by remote or automatic means.

Methods of draining a substance from a body cavity can also include methods of using the subject sheaths (described in greater detail below) with the subject surgical drains or other drains for draining a substance from a body cavity. The sheath of the subject invention can be placed around a surgical drain such as those disclosed in the present application, or the sheath can be placed around any suitable surgical drain, tube, or cannula. Methods of using the subject sheaths are described further below.

Figure 28:
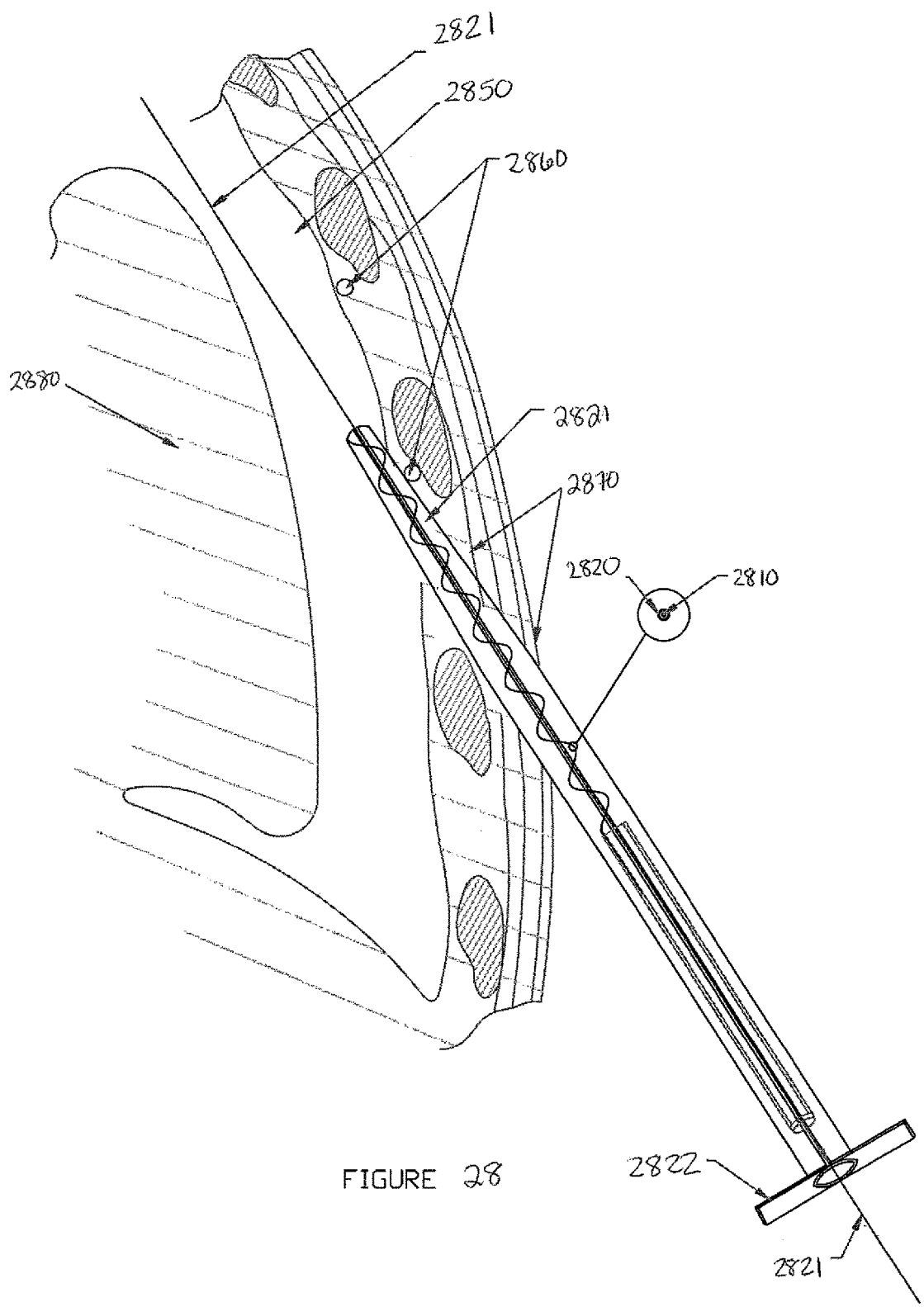
FIG. 28 provides a view of percutaneous insertion of a surgical drain, according to an embodiment of the invention.

FIG. 28 is a schematic of a subject surgical drain showing percutaneous insertion of the surgical drain. In this embodiment, the surgical drain is being introduced into the pleural cavity 2850 using implements for percutaneous insertion, including guidewire 2821 and introducer sheath 2822. The surgical drain tubing 2820 and preformed wire 2810 are also shown. In this embodiment, percutaneous insertion of the surgical drain can be performed using any suitable technique, such as the Seldinger technique. The guidewire is inserted through the needle after the local tract has been anesthetized. The anesthetized tract can then be dilated with dilators placed over a guidewire before inserting the small diameter introducer sheath 2822 over the guidewire 2821. The surgical drain can be placed into a body cavity while the surgical drain is still in the collapsed, or unsupported small diameter state, which allows for a smaller skin incision and a smaller tract through the tissue. After placement of the surgical drain into the thoracic cavity, the surgical drain can be expanded to larger diameter configuration. Also shown are skin and subcutaneous tissue 2870, intercostal nerve bundles 2860, pleural cavity 2850, and lung 2880.

The surgical drain in a larger diameter of the surgical drain in the expanded configuration allows the surgical drain to function like a large bore drain inserted in open procedures under general anesthesia. The larger diameter results in better drainage with more efficient evacuation of air, body fluids and or semi-solid or solid material than would be possible with a smaller diameter drain. When the desired function of the large diameter drain is no longer required, the surgical drain is withdrawn. The withdrawal process involves decreasing the diameter of the surgical drain by mediating the diameter-varying element (e.g., removing a preformed wire, or deflating a balloon, etc.). Once the surgical drain has reached the small diameter configuration, the surgical drain is removed.

The description of the present invention is provided herein in certain instances with reference to a subject or patient. As used herein, the terms "subject" and "patient" refer to a living entity such as an animal. In certain embodiments, the animals are "mammals" or "mammalian," where these terms are used broadly to describe organisms which are within the class mammalia, including the orders carnivore (e.g., dogs and cats), rodentia (e.g., mice, guinea pigs, and rats), lagomorpha (e.g., rabbits) and primates (e.g., humans, chimpanzees, and monkeys). In certain embodiments, the subjects, e.g., patients, are humans.

Sheaths

Aspects of the invention further include surgical sheaths. Sheaths for surgical drains according to certain embodiments of the invention are devices that are configured to be disposed around a cylindrical structure, such as a surgical drain. The sheaths can be used with the surgical drains of the subject invention, and they can also be used with other cylindrical structures such as surgical drains, tubes, catheters, cannulas, and the like. As with the subject surgical drains, the subject sheaths can be used in percutaneous, minimally invasive surgical, open surgical, or other interventional procedures.

Embodiments of the sheaths for surgical drains include a tubular structure with a proximal and a distal end, and a lumen. The tubular structure is configured to be disposed around a cylindrical structure, such as a surgical drain. By "cylindrical structure" is meant a catheter, cannula, tube, drain, etc. which has a cylindrical shape. In the discussion below, both the terms "tubular structure" and "sheath" will be used to refer to the sheath of the subject invention. By "disposed around" a cylindrical structure is meant that the tubular structure is configured to substantially surround the outer surface of a cylindrical structure, and is dimensioned such that is has sufficient length and diameter to surround the outer surface of the cylindrical structure. The tubular structure can be dimensioned to fit around a surgical drain without a significant gap between the surgical drain and the sheath, such that the sheath is closely applied to the outer surface of the surgical drain.

The tubular structure includes a distal end configured to be placed in a body cavity, such as a thoracic body cavity, and change in diameter when present in the body cavity from a first diameter to a second diameter that is smaller than the first diameter. The change in diameter of the distal end of the tubular structure is mediated by a diameter-varying element, described further below. The proximal end of the tubular structure is configured to be outside of the body when the distal end is present in the body cavity.

The tubular structure of the subject invention is therefore an element that can be disposed around a surgical drain, tube, cannula, etc., which has been placed in a body cavity. The tubular structure can therefore include an elongated structure. The body cavity can include, but is not limited to, any body cavity in need of draining, such as a thoracic body cavity, which includes a body cavity in the chest including a pleural body cavity, an abdominal body cavity, a gastrointestinal body cavity, a pelvic body cavity, a genitourinary body cavity, a cavity in the brain or spinal cord, a cavity in an extremity such as an arm or leg, etc. Further, the body cavity can be an anatomical or "natural" body cavity, e.g., the pleural space, or it can be a surgically-created or disease-created body cavity, e.g., an abscess cavity. As such, the dimensions of the tubular structure will vary depending on the dimensions of the surgical drain that it is used with. For example, a sheath configured to be disposed around an abdominal surgical drain can be longer than a surgical drain configured to drain a urinary bladder. Similarly, a tubular structure configured to surround a larger abdominal body cavity drain can have a larger diameter than a tubular structure configured to surround a smaller urinary bladder drain. Therefore, the length of the tubular structure is generally longer than that of the associated surgical drain, and may range from less than 1 cm to more than 400 cm, such as from 20 cm to 150 cm, and including from 20 cm to 40 cm.

The lumen in the tubular structure is dimensioned to fit around a surgical drain without a significant gap between the surgical drain and the sheath, such that the sheath is closely applied to the outer surface of the surgical drain. As such, the inner diameter of the lumen will vary depending on the size of the surgical drain. Therefore, the inner diameter of the tubular structure may range from less than 1 mm to more than 5 cm, such as from 3 mm to 2 cm, and including from 5 mm to 10 mm.

The sheath can be made of any suitable biocompatible materials with a low coefficient of friction such as polymers including but not limited to polyvinylchloride, polyurethane, polyethylene, polypropylene, polyamides; polymers which can be degraded by electromagnetic radiation, or laser light, biodegradable materials, plastic, silicone, metals; metal alloys; and combinations thereof. The sheath can further have one or more fenestrations to allow drainage.

The tubular structure has a distal end that is configured to be placed into a body cavity. The tubular structure has a proximal end that is configured to be outside of the body when the distal end is present in the body cavity.

The tubular structure can be placed around a surgical drain before the surgical drain is placed in the body cavity. In some embodiments, the tubular structure which is disposed around a surgical drain may be configured to have a smaller diameter prior to insertion, and be configured to have a larger diameter when present in the body cavity. In embodiments where the sheath is constructed of biodegradable materials, the sheath can provide cushioning for an indwelling drain, and collapse after withdrawal of the enclosed drain. The sheath formed of biodegradable material simply stays painlessly collapsed within the body or alternatively remains in place until absorbed by the patient rather than be withdrawn.

The tubular structure in some embodiments can be secured to a surgical drain. In some embodiments, the proximal end of the tubular structure is secured to the proximal end of the elongated structure, and in some embodiments, the distal end of the tubular structure is secured to the distal end of the elongated structure. In some embodiments, the tubular structure can be secured to the surgical drain in more than one location, e.g., at both ends of the surgical drain.

By "secured" to a surgical drain is meant attaching the tubular structure, or sheath, to a surgical drain using any suitable securing means, such as with a clip, a suture, simple surgical ligature, an adhesive, etc. In some embodiments, more than one method of securing can be used. As discussed above, the tubular structure can be secured to an elongated structure of the subject invention, and the tubular structure can also be secured to any suitable cylindrical structure such as any surgical drain, tube, catheter, cannula, etc.

As discussed above, the sheaths of the subject invention can include a diameter-varying element, which is an element that can significantly change the diameter of the subject sheath. In addition to the ability to change the diameter of a surgical drain, the diameter-varying element can provide hoop strength. By hoop strength is meant the ability of a drain or tube to withstand pressure, bending or crushing forces. The diameter-varying element can change the sheath of the subject invention from a larger diameter, which is referred to as an "expanded" state, to a smaller diameter, which can be referred to as a "collapsed" state. By "significantly change the diameter" of the sheath of the subject invention is meant a change in diameter of at least 20%, such as at least 30%, or at least 40%, or more than 50%, more than 70%, more than 80%, more than 90%, or more than 99% etc. In some embodiments, the significant change in diameter can be a decrease in diameter, and in some embodiments, the significant change in diameter can be an increase in diameter.

The sheath may or may not include a diameter-varying element. The diameter-varying element as present in a sheath can be a wire, or a balloon filled with a fluid, which embodiments are discussed further below. As such, the diameter-varying element is an element that can be inserted into or removed from a sheath (e.g., a wire), or it can be an element that is altered when present in the sheath (e.g., a balloon that is filled with a liquid). As such, the diameter-varying element can be present in a sheath when the sheath is placed in a body cavity, or the diameter-varying element can be placed into a sheath after the sheath has been placed in a body cavity. The diameter-varying element, when present, may or may not be integrated with the subject sheath. By integrated is meant that the diameter-varying element cannot be separated from the tubular structure without irreparably altering the tubular structure.

For example, in some embodiments, the diameter-varying element is an element that maintains the sheath in a larger diameter (e.g., a preformed wire), which decreases to a smaller diameter once the diameter-varying element is removed. In other embodiments, the diameter-varying element is an element that can change the diameter of a sheath from a larger diameter to a smaller diameter (e.g., a straight wire inserted into preformed spiral tubing) once the diameter-varying element is inserted. In yet another embodiment, the diameter-varying element is altered when present in a sheath to decrease the diameter of the sheath before removal (e.g., a balloon that can have the air removed).

In some embodiments, there can be more than one diameter-varying element in a sheath, or more than one type of diameter-varying element in sheath. In other embodiments, the tubular structure may be configured to have a smaller diameter prior to insertion, and be configured to have a larger diameter when present in the body cavity.

The diameter-varying element has a length sufficient to extend at least along the portion of the sheath that is inside the body cavity, such that the diameter-varying element provides a segment of the distal end of the sheath which can significantly change in diameter when present in the body cavity. For example, in certain embodiments, the diameter-varying element is present in the distal one third of a sheath. In some embodiments, the diameter-varying element is present in the distal half of a sheath. In some embodiments, the diameter-varying element is present along the entire length of the sheath. Therefore, the length of the diameter-varying element may range from less than 1 cm to more than 400 cm, such as from 20 cm to 150 cm, and including from 20 cm to 40 cm.

The diameter-varying element as embodied in a sheath may be present in the wall of the sheath. By "wall" of the sheath is meant the portion of the tubular structure which surrounds the surgical drain. In this embodiment, the tubular structure can have one or more fenestrations in the wall to allow for drainage of body fluids through the wall of the tubular structure. In other embodiments the "wall" can have a spiral configuration. In this embodiment, the "wall" of the tubular structure is more of a support, in that the "wall" is not a continuous wall, but rather is a support structure which, once placed in a body cavity, allows "walls" to be formed by the body tissue which surround the structure. For example, the "wall" of the tubular structure may be formed of tubing in a spiral configuration, which may have a diameter-varying element inside the tubing (e.g., a wire)

Figure 16:
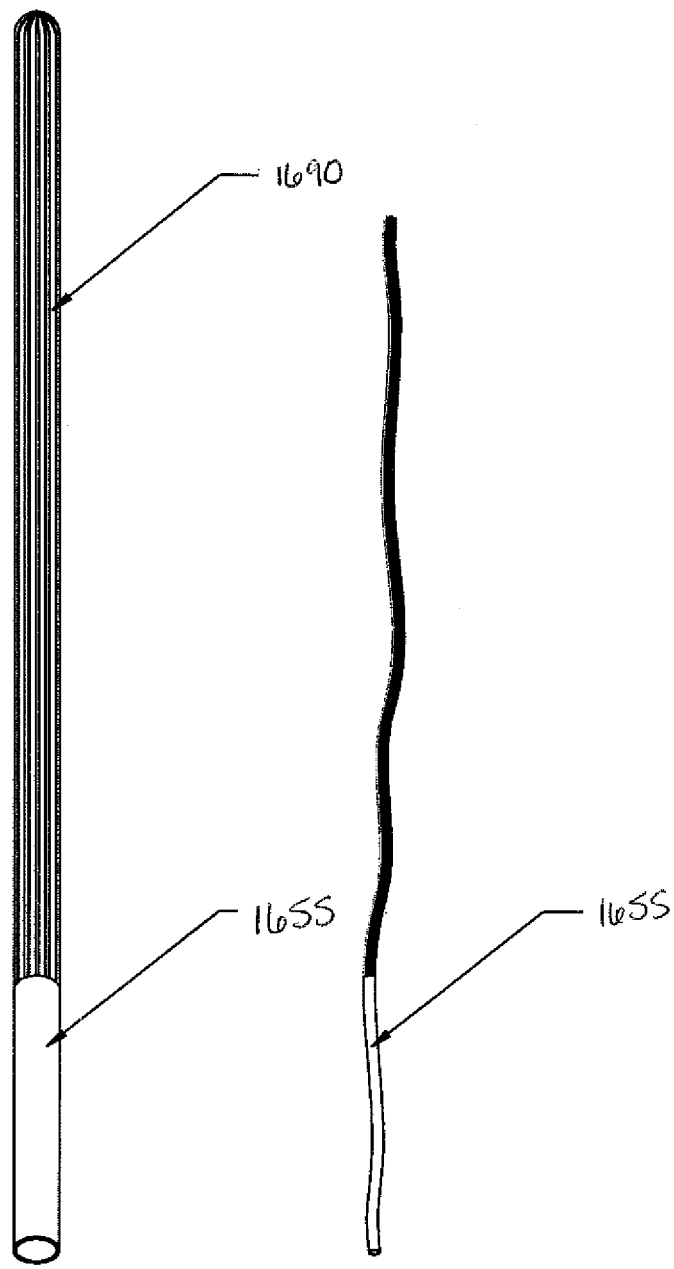
FIGS. 16A and 16B provide views of a sheath for a surgical drain in both an expanded and a collapsed configuration, according to an embodiment of the invention.

FIGS. 16A and 16B show an embodiment of a sheath 1655 according to the invention. The sheath 1655 is configured such that any suitable surgical drain, tube, catheter or cannula can be inserted into the sheath (not shown). In FIG. 16A, the sheath in an expanded configuration is shown, e.g., with inflated balloons 1690 in the wall of the sheath. In FIG. 16B, the sheath is shown in a collapsed configuration, in which the diameter-varying element, e.g., balloons, have been deflated by aspirating air, foam, liquid, etc. In this embodiment, the diameter-varying element is present along the entire length of the sheath, such that the entire diameter of the sheath is decreased.

In some embodiments of the invention, as with the surgical drain discussed above, the sheath may further comprise branches. By "branches" or "limbs" is meant one or more extensions, or limbs, of the main portion of the sheath that can be configured to be disposed around a branched surgical drain, such as a surgical drain of the subject invention. For example, in draining a body cavity in the chest, one branch or limb of a surgical drain can be placed in the upper portion of the chest, and another branch of the surgical drain can be placed at the base of the chest. A sheath configured to surround a surgical drain of the subject invention can therefore have two or more branches, or three or more branches, or four or more branches, etc. The branches may, in some embodiments, have a diameter that is smaller than the diameter of the proximal portion of the sheath.

Figure 17:
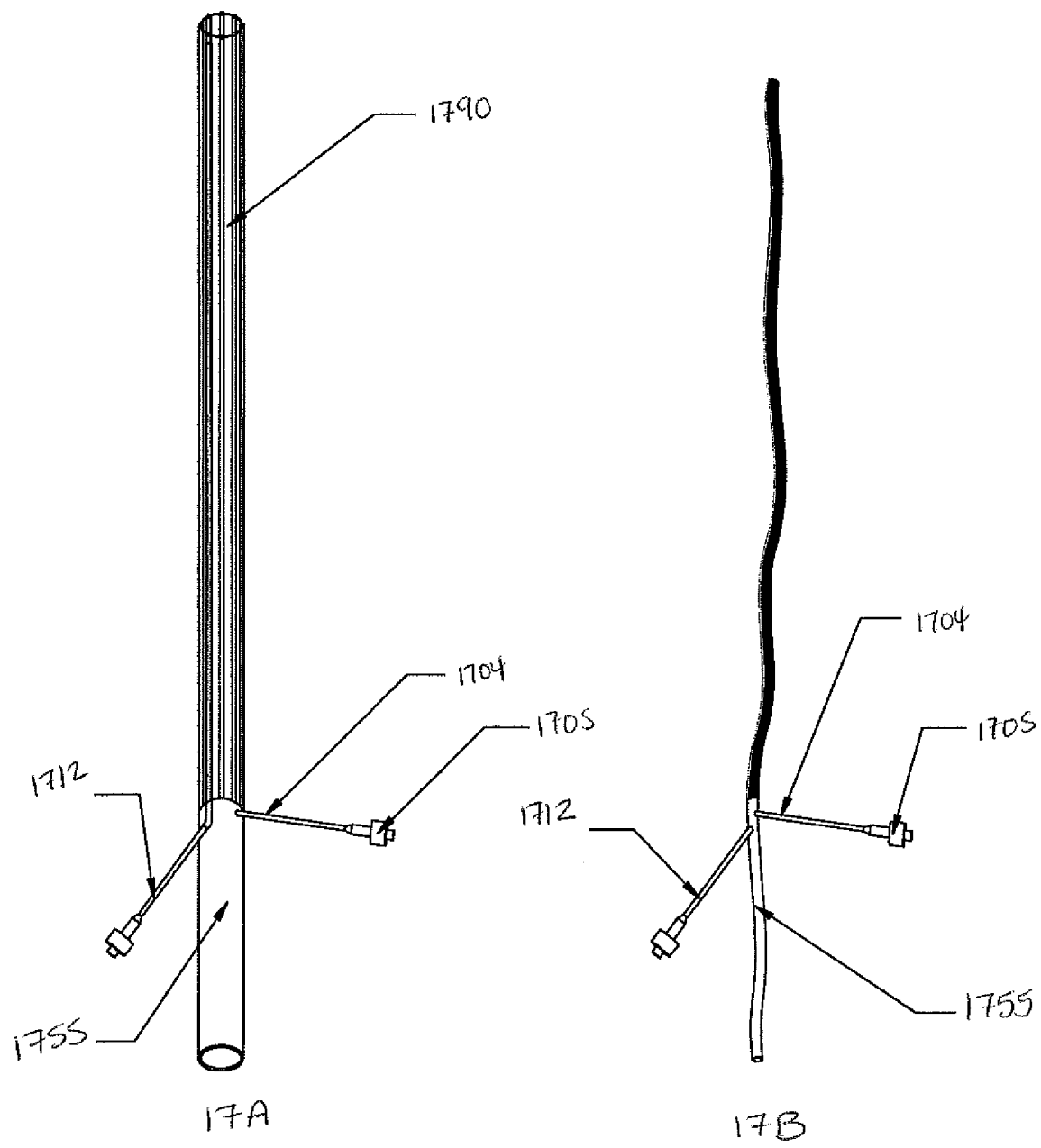
FIGS. 17A and 17B provide additional views of a sheath for a surgical drain in both an expanded and a collapsed configuration, according to an embodiment of the invention.

As summarized above, sheaths of the invention may include a diameter-varying element. FIGS. 17A and 17B show views of an embodiment of a sheath of the invention where the sheath includes a diameter-varying element in the form of a plurality of parallel balloons. FIG. 17A shows the expanded configuration of the sheath, with the balloons 1790 inflated with sheath 1755 cushioning the effects of the drain (not shown). The balloons are inflated via one-way valve 1705 and tubing 1704. Also shown is tubing 1712 for a drug delivery lumen, discussed further below. FIG. 17B illustrates the collapsed form of the sheath 1755, prior to withdrawal.

Figure 18A:
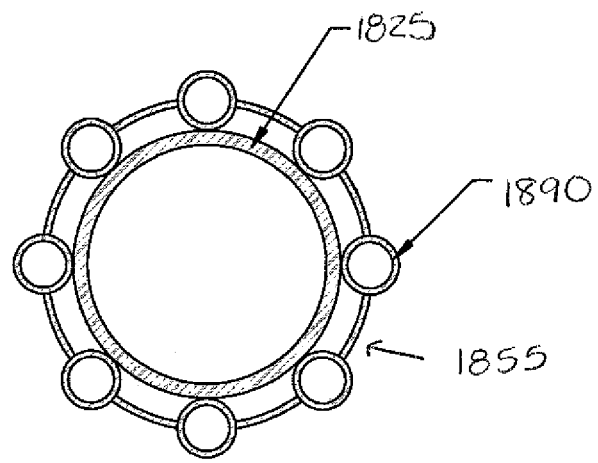
FIGS. 18A and 18B provide detailed views of a sheath for a surgical drain, according to an embodiment of the invention.
Figure 18B:
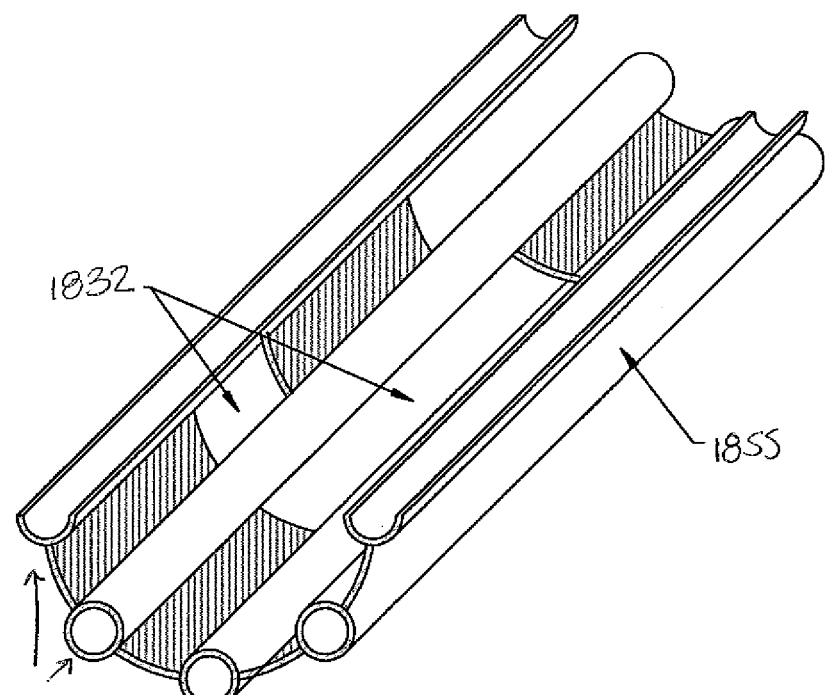
Figure 20:
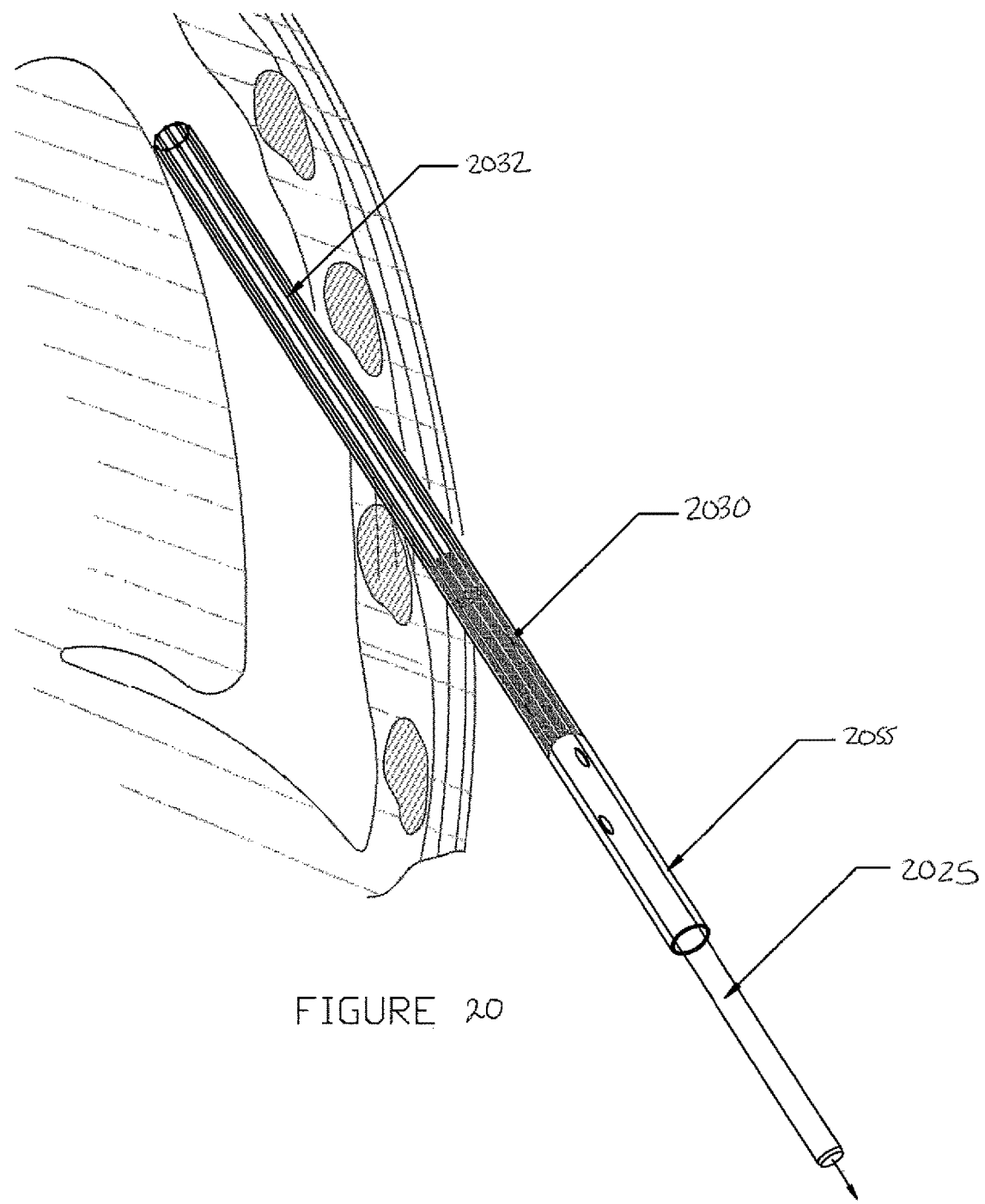
FIG. 20 provides another view of the sheath in an expanded configuration placed over a surgical drain, as the surgical drain is being withdrawn, according to an embodiment of the invention.
Figure 21:
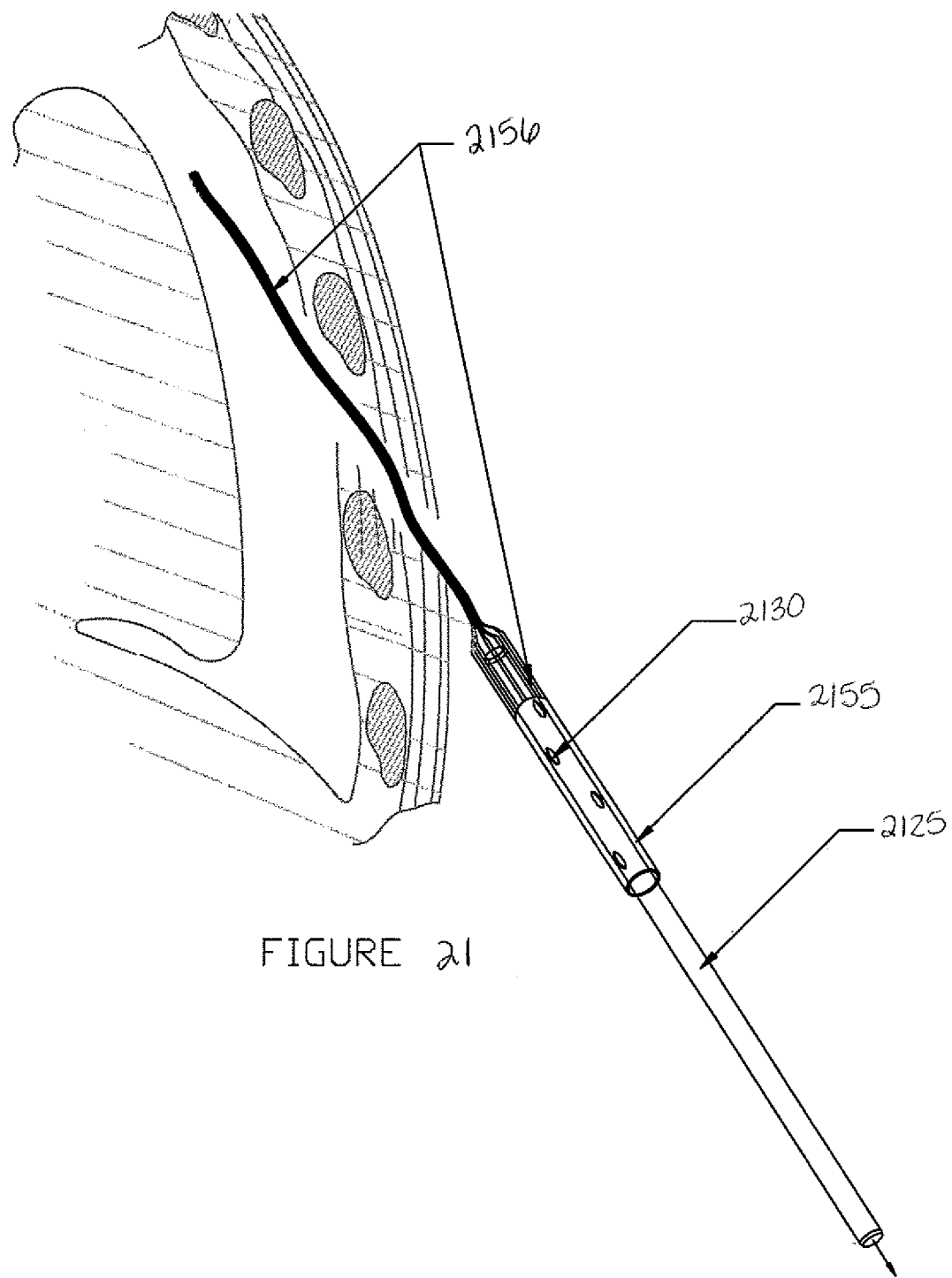
FIG. 21 provides a view of a sheath for a surgical drain in a collapsed configuration, as the surgical drain is being withdrawn, according to an embodiment of the invention.

FIGS. 18A and 18B illustrate an embodiment of the sheath 1855, where the sheath includes a diameter-varying element in the form of balloons. FIG. 18A shows a cross-sectional view of the sheath. FIG. 18B shows a cutaway view of this embodiment of the subject sheath, showing sheath 1855 with balloons 1890 and fenestrations 1832. In this embodiment, the balloons 1890 are potential space, which can be filled by air, gas, self-inflating foam, etc., which allows for cushioning the tissues from the pain while surgical drain 1825 is indwelling. At time of withdrawal of the drain, the balloons 1890 in the sheath 1855 can be left inflated or deflated depending on operator preference, as shown in FIGS. 20 and 21 (described below). However, at the time of withdrawal of the sheath, the balloons can be deflated via application of suction to the balloons through a one-way valve. Deflating the balloons will decrease the overall diameter of the surgical drain and sheath combination, and decrease the pain of withdrawal. Furthermore, deflation of the sheath can increase the safety of the procedure for the patient, as the ingress of air during withdrawal is less likely through the deflated sheath. In another embodiment, the potential space of the balloons can be filled by self-inflating spongiform foam of various possible materials.

Figure 19:
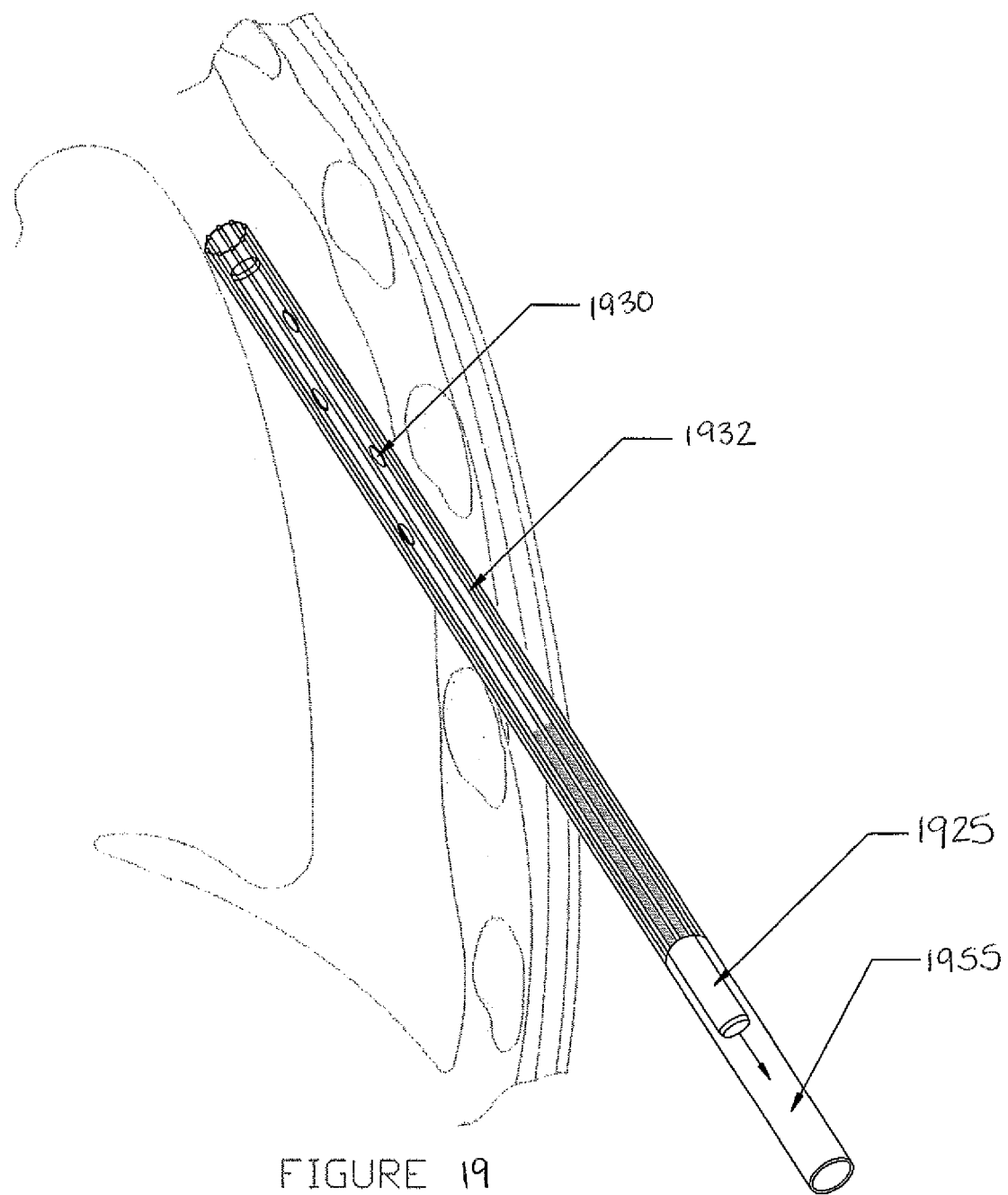
FIG. 19 provides a view of the sheath in an expanded configuration placed over a surgical drain, according to an embodiment of the invention.

FIG. 19 illustrates another embodiment of the sheath, showing employment of the sheath 1955 over a surgical drain 1925 which has been placed in the thoracic cavity. The inflated balloon sheath 1955 allows the drain 1925 to drain via the fenestrations 1932 in the sheath and the fenestrations 1930 in the drain itself.

In FIG. 20, the surgical drain is being withdrawn from the chest while the balloons in sheath 2055 are inflated. In this embodiment, inflation of the balloons in the sheath can cushion the tissues from the pain of the drain 2025 being withdrawn. Also shown in this figure are fenestrations 2032 in the sheath and fenestrations 2030 in the drain.

Alternatively, FIG. 21 shows withdrawal of the surgical drain in which the balloons of the sheath that surround the surgical drain 2125 have been deflated. In this embodiment, the deflation of the balloons in the sheath 2155 reduces the diameter of sheath, shown as element 2156, which can both decrease the pain of withdrawal and increase the safety of the procedure. Ingress of air during withdrawal is less likely through a deflated sheath 2156.

Figure 22:
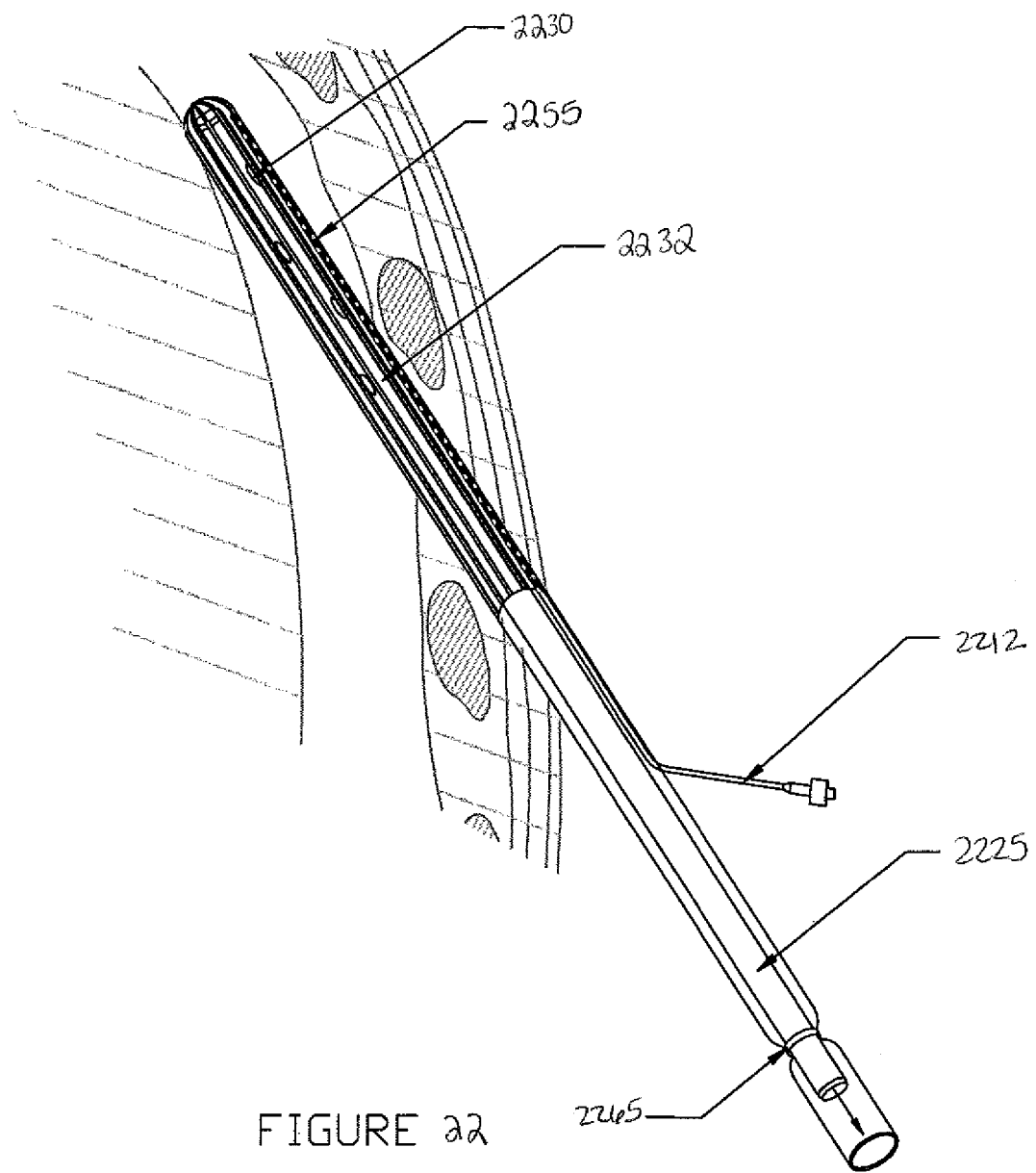
FIG. 22 provides a view of a sheath for a surgical drain, where the sheath is fixed at the proximal end of the drain, according to an embodiment of the invention.

As discussed above, the sheath can be secured to a surgical drain at the proximal end of the drain, or the distal end of the drain. FIG. 22 illustrates the embodiment in which the operator has chosen to fix the sheath 2255 to the drain 2225 at the proximal end of the drain, or the end farthest from the patient. In this embodiment, the sheath is fixed to the surgical drain with a securing means 2265. The sheath can be secured to any suitable surgical drain, or can be attached to a surgical drain of the subject invention, using any suitable means.

Figure 23:
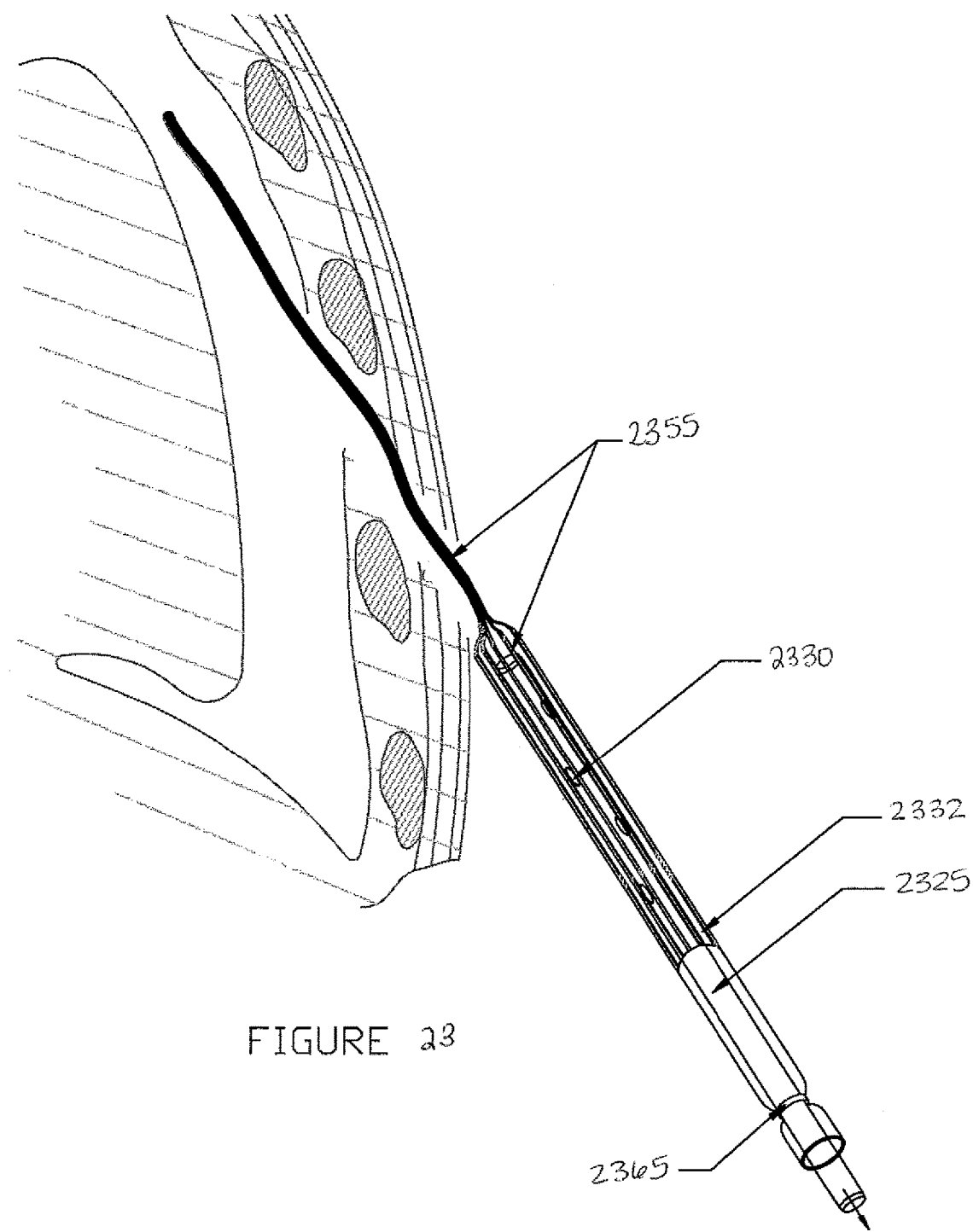
FIG. 23 provides a view of a sheath for a surgical drain, where the sheath is fixed at the proximal end of the drain, as the surgical drain is being withdrawn, according to an embodiment of the invention.

FIG. 23 illustrates the drain 2325 slipping through sheath 2355 and out of the patient. The sheath in this embodiment is fixed at the proximal end with securing means 2365, and would therefore simply follow the removal of the surgical drain. The sheath would be withdrawn in a collapsed state after the excess length of sheath 2355 relative to the drain 2325 is exhausted. The collapsed sheath is smaller in diameter and has no rigid structure of its own, which would minimize the pain and narcotic medication requirement of the withdrawal process.

Figure 24:
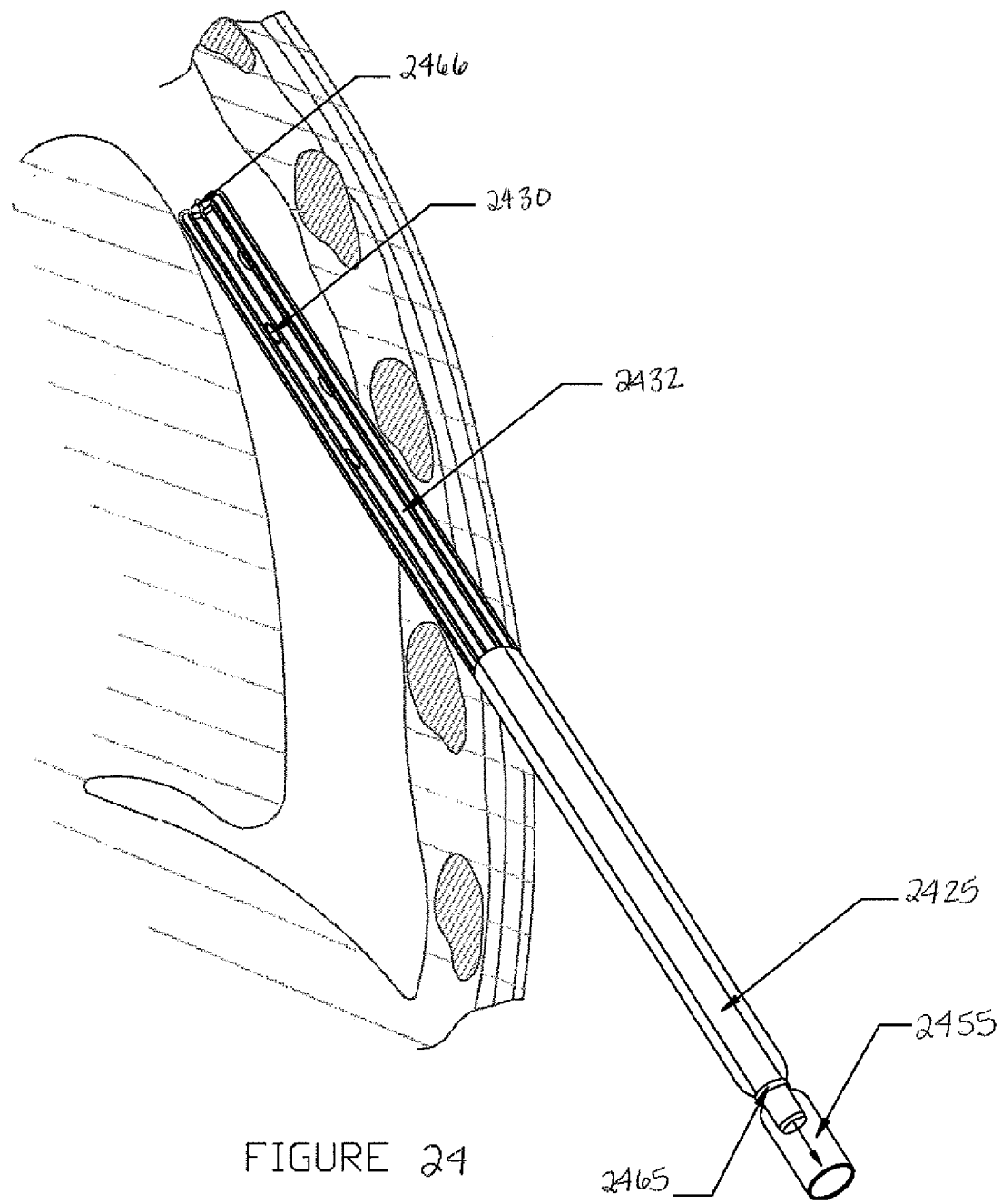
FIG. 24 provides a view of a sheath for a surgical drain, where the sheath is secured to a surgical drain, according to an embodiment of the invention.

FIG. 24 illustrates another embodiment of a sheath 2455 where the operator (e.g., a surgeon) chooses to fix the sheath to the indwelling surgical drain 2425 at the distal end 2466 of the drain and sheath. In this embodiment, the sheath is also shown as being secured to the surgical drain at the proximal end with securing means 2465.

Figure 25:
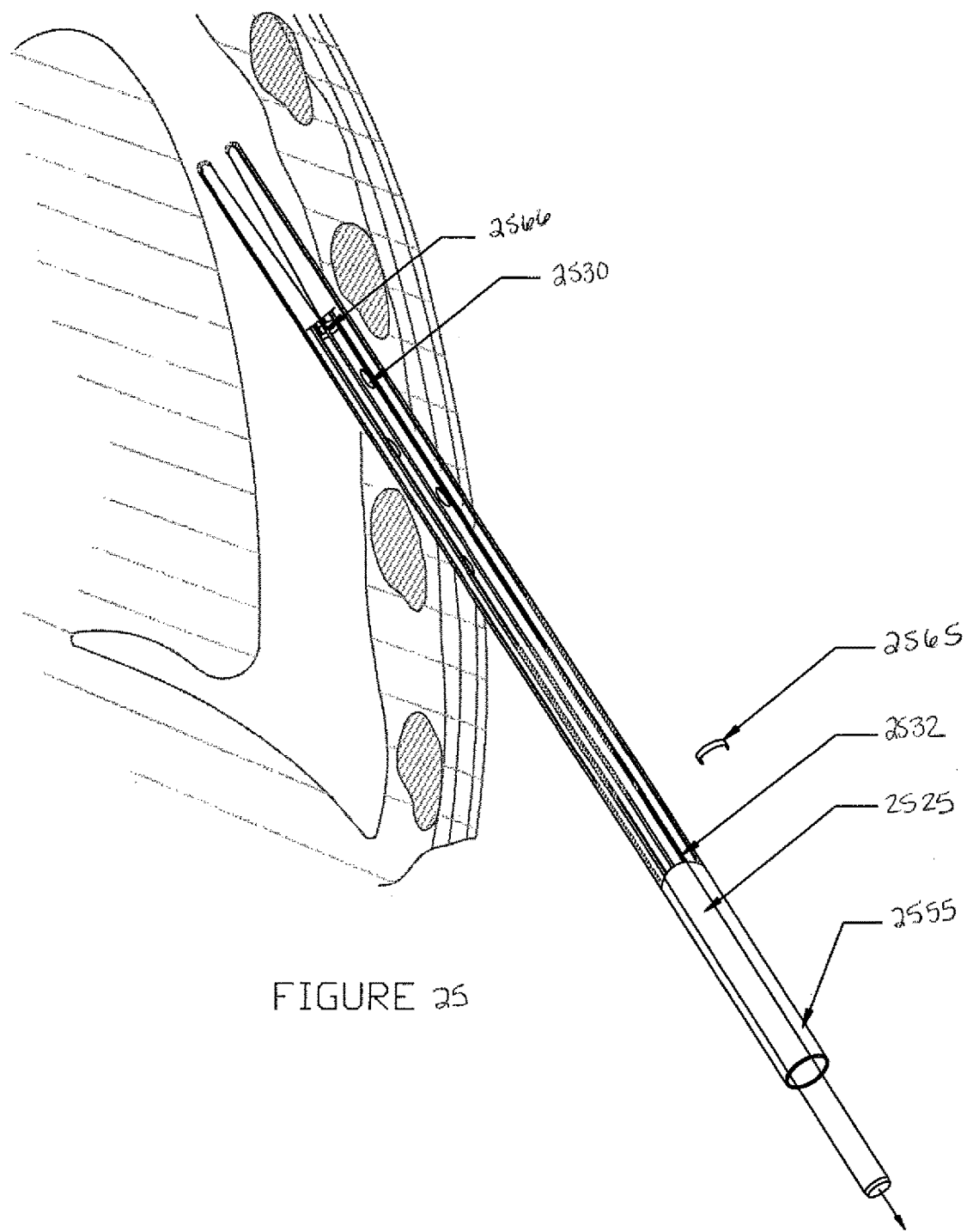
FIG. 25 provides a view of a sheath for a surgical drain, where the sheath is fixed at the distal end of the drain, as the surgical drain is being withdrawn, according to an embodiment of the invention.

FIG. 25 illustrates a similar embodiment to that shown in FIG. 24, illustrating how when the drain 2525 is withdrawn while the sheath is secured to the distal end of the drain, shown as element 2566, the drain 2525 will slip through the sheath 2555 as it is initially withdrawn. Also shown is removal of proximal fixation element 2565. As the surgical drain is withdrawn further, the sheath will follow, which allows for the reduction of friction while the surgical drain and sheath are removed. Also shown are fenestrations in the surgical drain 2530, and fenestrations in the sheath 2532.

The sheath of the subject invention can also include a coating around a surface of the sheath. By "coating" is meant a substance that is applied to a surface of a sheath. In some embodiments, the coating may be a coating that reduces friction, such as a friction-reduction coating, or it may be a coating that contains a pharmaceutical agent, e.g. an agent that decreases the risk of blood clot formation, a coating that decreases the risk of infection, a coating that decreases pain, etc. In some embodiments, the sheath may include a friction-reduction coating. Substances that may be used in a friction-reduction coating can include but are not limited to: low friction polymers such as fluoro-ethylene co-polymer (FEP), other low friction coatings that include paralyne, silicone, Teflon® coating, etc. The presence of a friction-reduction coating on the outside of a sheath can decrease patient discomfort with removal of the sheath. The presence of a friction-reduction coating on the inside surface of a sheath can also improve the function of the surgical drain, by decreasing the chances of a surgical drain becoming clogged by draining substances. A friction-reduction coating on the inside surface of a sheath could also the diameter of a surgical drain to be reduced while preserving the same capacity for drainage.

In some embodiments of the invention, the sheath includes, in addition to the lumen configured to be disposed around a surgical drain, an additional lumen in the wall of the sheath configured to deliver a substance into the body cavity. Substances that can be delivered into the body cavity through an additional lumen can include pharmaceutical agents such as antibiotics, anti-clotting agents, anesthetic agents, etc. Pharmaceutical agents can be administered while the sheath is in place, for example, they can be administered continuously or intermittently for therapeutic treatment of infection, for example. In other embodiments, pharmaceutical agents can be administered in a single dose, for example, if it is desired to administer an anesthetic agent along the tract of the sheath prior to withdrawal of the sheath. In some embodiments, there can be more than one lumen. The lumen configured for delivery of a therapeutic substance, such as a pharmaceutical agent, can have a valve on the end, and can be attached to a syringe for delivery of the agent. As with drains of the invention, e.g., as described above, this lumen may be in fluid communication with a source of the agent, such as in fluid communication with a source of the agent positioned at the proximal end of the sheath.

Figure 26:
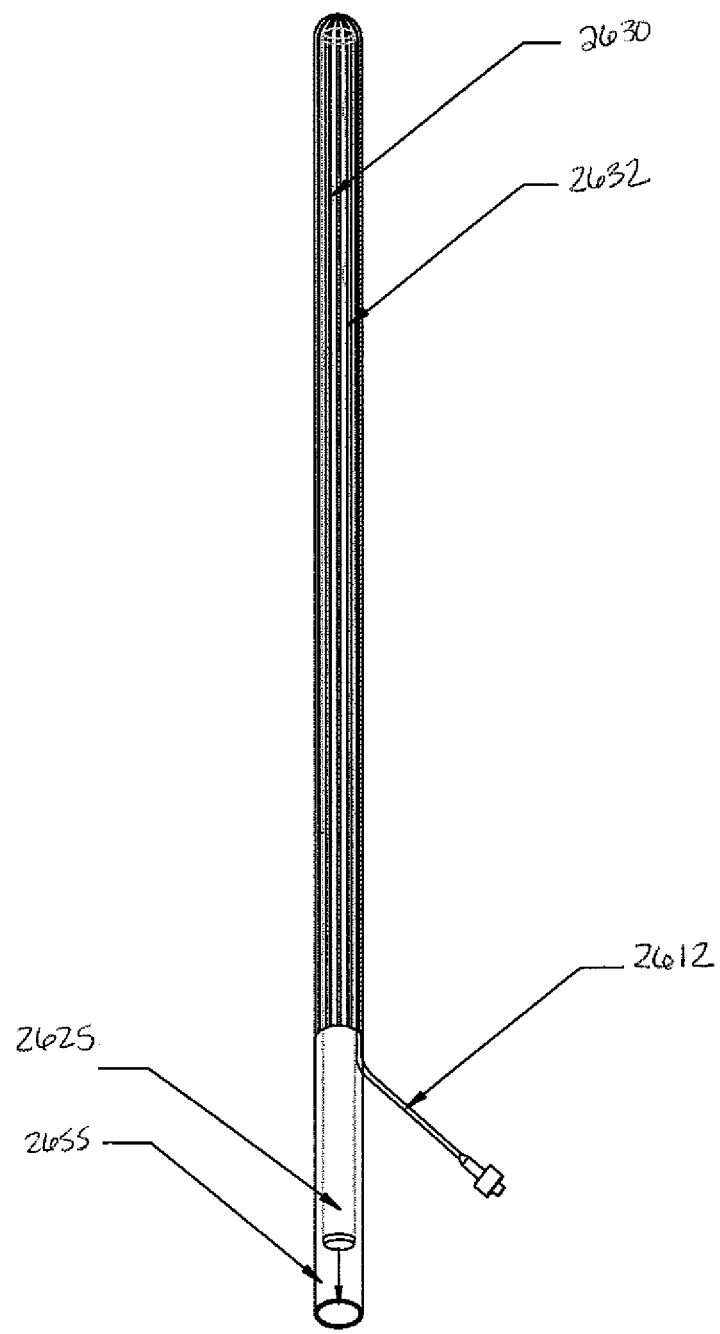
FIG. 26 provides a view of a sheath for a surgical drain, with an additional lumen in the wall of the sheath, according to an embodiment of the invention.
Figure 27:
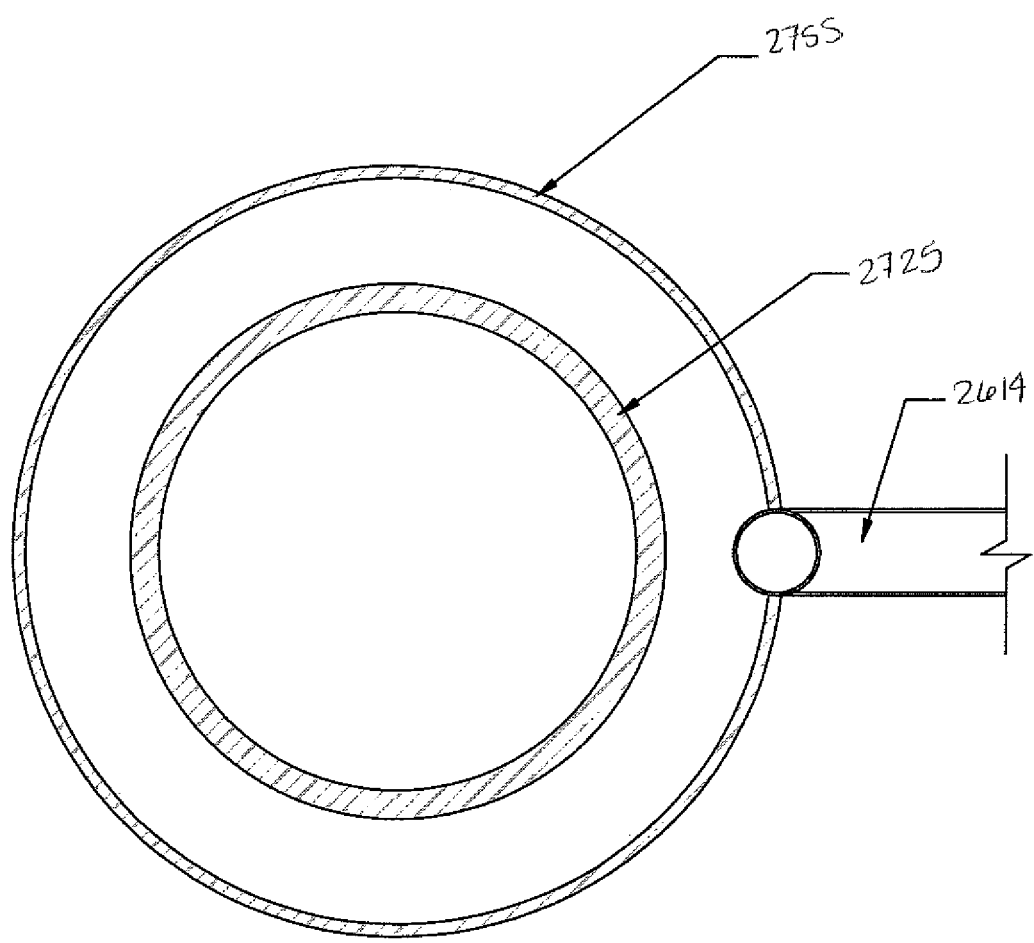
FIG. 27 provides a cross-sectional view of the sheath for a surgical drain in FIG. 26, according to an embodiment of the invention.

FIG. 26 and FIG. 27 show an embodiment of the subject sheath that shows the incorporation of tubing 2612 into the device. The tubing 2612 may be present throughout the entire length of the sheath 2655, or the tubing may be present only in a portion of the device, e.g., in the proximal third, or the proximal half of the sheath, etc. A cross-sectional view of the sheath 2655 with the delivery lumen 2614 is shown in FIG. 27. Medications to treat disease may be given via tubing 2612. Fenestrations 2632 present in the sheath 2655 that is employed over surgical drain 2625 can allow for the dispersal of medications of therapeutic value to the space in the body cavity that is drained by the device. Or the same delivery system would aid in pain control by delivering topical anesthetic medication during the period of drain use and or in preparation for withdrawal.

Also of interest are sheaths that provide cushioning for a surgical drain, tube, cannula, catheter etc. Embodiments of a cushioning sheath can include a sheath where the wall of the sheath includes an inner and outer layer, and the space between is filled with a cushioning material. Cushioning material can include foam, such as a self-inflating foam, a fluid such as air or liquid, etc., or any other suitable cushioning material. In some embodiments, a cushioning sheath may have a wall formed of a single layer, however the wall can be constructed such that the wall is thick enough to provide cushioning for an enclosed drain. In some embodiments, a sheath can have both a wall with inner and outer layers thick enough to provide cushioning, and also have the space between the inner and outer layers of the wall be filled with a cushioning material, such as foam. The sheath as in this embodiment can be constructed of any suitable biocompatible materials as disclosed above. A sheath of this embodiment may or may not have one or more fenestrations to allow drainage. A cushioning sheath of this embodiment may not have a separate diameter-varying element, however may passively collapse or decrease in diameter upon removal of the encased surgical drain or tube.

Methods of Using a Sheath

Methods of draining a substance from a body cavity can include methods of using the subject sheaths with surgical drains to drain a substance from a body cavity. The sheath of the subject invention can be placed around a cylindrical structure including a surgical drain such as those disclosed in the present application, or the sheath can be placed around any suitable surgical drain, tube, catheter, or cannula. The methods of using the subject sheaths can also include manufacturing a subject sheath such that it is disposed around any surgical drain, which can include a surgical drain of the subject invention. The methods can also include positioning a surgical drain in a body cavity, where the surgical drain has been manufactured as above to include a sheath of the subject invention. Methods can also include placing a subject sheath around a surgical drain prior to positioning the surgical drain in a body cavity.

The subject sheaths can be manufactured such that the sheath is disposed around a surgical drain. In some embodiments, the sheath is not secured to a surgical drain. In other embodiments, the sheath can further be secured to the surgical drain (e.g., at the proximal end, or at the distal end) at the time of manufacture. In some embodiments, the sheath can be secured at more than one location, e.g., at the proximal end and the distal end. In some embodiments, the surgical drain that is used can be a surgical drain of the subject invention.

The methods can also include the positioning of a surgical drain in a body cavity, where the surgical drain has been manufactured as disclosed above to include a sheath of the subject invention. As such, the method can include positioning the combination surgical drain and sheath in a body cavity simultaneously. In some embodiments, the surgical drain can be a surgical drain of the subject invention.

Methods can also include placing a subject sheath around a surgical drain prior to positioning the surgical drain in a body cavity. As such, the methods can include placing a tubular structure around the outer surface of an elongated structure, and then positioning the distal end of the elongated structure and the tubular structure in a body cavity. For example, a subject sheath may be provided in a kit, which can also include a surgical drain. In this example, the method can include placing the sheath around the outer surface of a surgical drain, and positioning the surgical drain in a body cavity (e.g., by a surgeon in an operating room). In some embodiments, the surgical drain can be a surgical drain of the subject invention.

The methods can also include securing the sheath to the surgical drain. As such, the methods can include securing the tubular structure a surgical drain, e.g., an elongated structure of the subject invention. The tubular structure can be secured to the elongated structure at the distal end, such that the distal end of the tubular structure is secured to the distal end of the elongated structure. The tubular structure can also be secured to the elongated structure at the proximal end, such that the proximal end of the tubular structure is secured to the proximal end of the elongated structure. The tubular structure can also be secured to a sheath in a location between the proximal and distal ends, such as halfway between the proximal end and the distal end. As disclosed above, by "securing" is meant any suitable means for fixing or attaching a sheath to a surgical drain, such as by clipping, suturing, use of an adhesive, etc.

In embodiments in which a sheath has been secured to a surgical drain, the methods can include removing the sheath along with removing the surgical drain. In embodiments where the sheath is secured to a surgical drain at the proximal or the distal end, both the sheath and the surgical drain can be removed by pulling the surgical drain out of the body cavity. In one embodiment, if the sheath is secured to the surgical drain at the distal end of the surgical drain, the surgical drain can be removed, and as the distal end of the surgical drain is removed, the attached sheath will follow. Therefore, in embodiments in which the surgical drain is an elongated structure of the subject invention, the method can include removing a tubular structure secured to the distal end of the elongated structure, such that the tubular structure is removed after the elongated structure has been removed.

In another embodiment, if the sheath is secured to the surgical drain at the proximal end of the surgical drain, the surgical drain can be removed, and as the proximal end of the surgical drain is removed, the attached sheath is removed along with the surgical drain. Therefore, in embodiments in which the surgical drain is an elongated structure of the subject invention, the method can include removing a tubular structure secured to the proximal end of an elongated structure, such that the tubular structure is removed at the same time as the elongated structure is removed.

The sheaths of the subject invention can be used with any suitable drain, tube, catheter, cannula, or other cylindrical structure, etc., used for any suitable purpose including but not limited to draining a body cavity, administering a pharmaceutical agent, perfusion, etc. The subject sheath, during use, can be maintained in the larger diameter while the distal end is present in the body cavity in order to provide cushioning for an indwelling drain, tube, catheter, cannula, etc. In addition, the sheath can be maintained in the larger diameter while it is placed around the outer surface of a drain or tube in order to allow for the largest diameter for the underlying drain or tube. Prior to removal of the sheath, with or without the underlying drain or tube, the diameter of the distal end of the sheath can be decreased, which allows for easier removal of the sheath. Prior to insertion of the sheath, in embodiments in which the sheath is disposed around the outer surface of a cylindrical structure such as a surgical drain, the sheath can be present in the smaller, or collapsed configuration, such that the sheath and surgical drain can be inserted through a smaller skin incision, for example. In some embodiments, the diameter of the sheath can remain in the expanded configuration during removal of the underlying drain or tube, in order to cushion the surrounding tissues during withdrawal of the underlying drain or tube.

As discussed above, the change in diameter of the distal end of the sheath may be mediated by a diameter-varying element. In some embodiments, the diameter-varying element is present in the wall portion of a sheath and is altered before the sheath is removed from the body cavity. For example, in the case of a sheath in which the diameter-varying element includes one or more balloons filled with foam in the wall portion, the filled balloons in the wall result in an expanded wall portion of the sheath, and therefore a larger diameter of the sheath. Once the foam or air within self-expanding foam is removed from the balloons, the sheath will decrease in size, thereby decreasing the overall diameter of the sheath.

Figure 29:
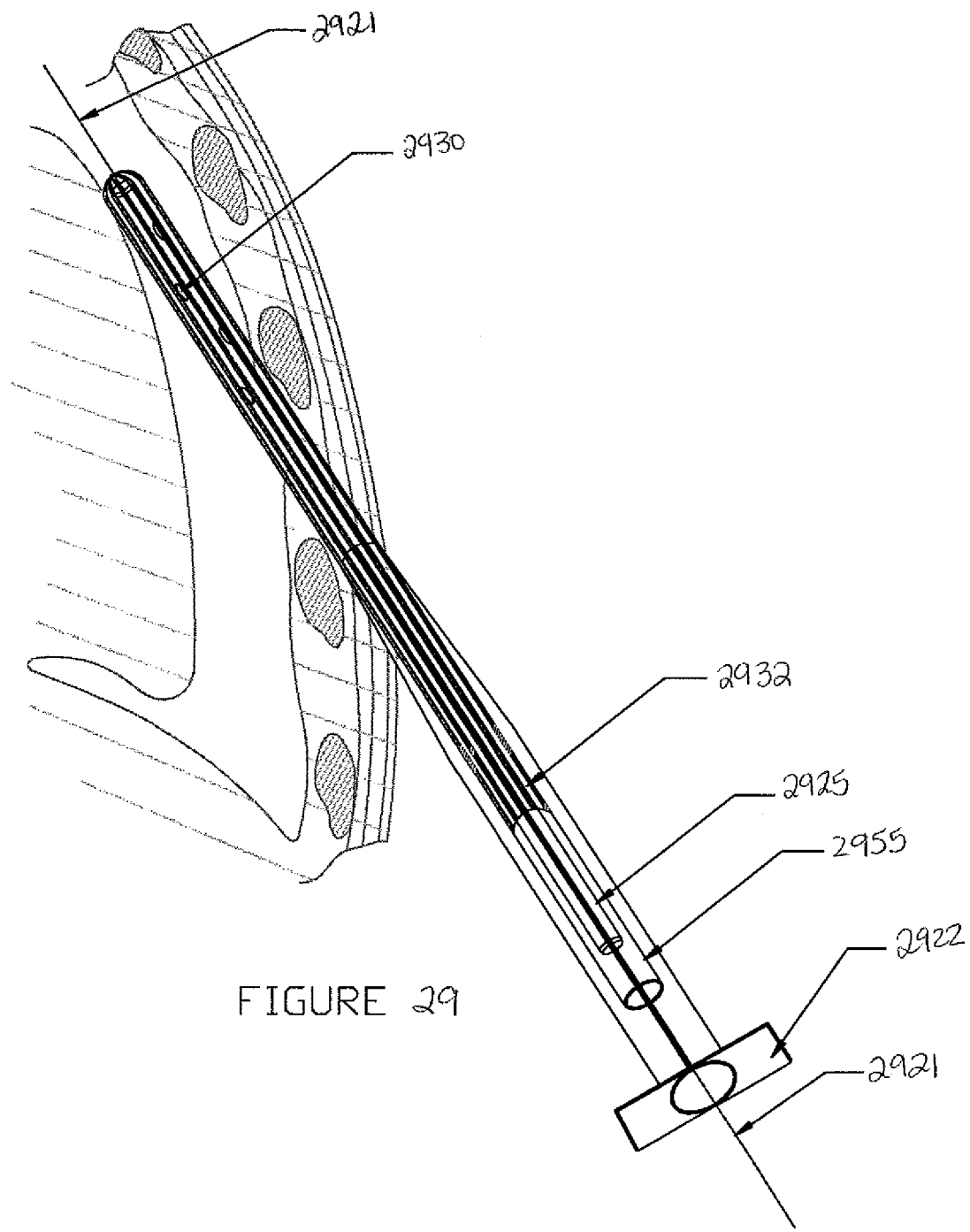
FIG. 29 is another embodiment of percutaneous insertion of a surgical drain and sheath, according to an embodiment of the invention.

FIG. 29 is a schematic of percutaneous insertion of a sheath which has been placed over a surgical drain. In this embodiment, the combined sheath 2955 and surgical drain 2925 are being introduced into the pleural cavity using implements for percutaneous insertion, including guidewire 2921 and introducer sheath 2922. In this embodiment, percutaneous insertion of the sheath and surgical drain can be performed using any suitable technique, such as the Seldinger technique. The guidewire is inserted through the needle after the local tract has been anesthetized. The anesthetized tract can then be dilated with dilators placed over a guidewire before inserting the small diameter introducer sheath 2922 over the guidewire 2921. The sheath and surgical drain can be placed into a body cavity while the sheath is in the collapsed, or unsupported small diameter state, which allows for a smaller skin incision and a smaller tract through the tissue. After placement of the sheath and surgical drain into the thoracic cavity, the sheath can be expanded to larger diameter configuration (e.g., by inflating balloons in the wall of the sheath).

Use of the sheath while the surgical drain is indwelling can decrease the discomfort associated with an indwelling drain. Furthermore, in some embodiments, when it is time to remove the drain, the diameter of the sheath can be decreased by mediating the diameter-varying element (e.g., removing foam or liquid from a balloon, etc.). Once the sheath has reached the small diameter configuration, the sheath and surgical drain can be removed.

The description of the present invention is provided herein in certain instances with reference to a subject or patient. As used herein, the terms "subject" and "patient" refer to a living entity such as an animal. In certain embodiments, the animals are "mammals" or "mammalian," where these terms are used broadly to describe organisms which are within the class mammalia, including the orders carnivore (e.g., dogs and cats), rodentia (e.g., mice, guinea pigs, and rats), lagomorpha (e.g., rabbits) and primates (e.g., humans, chimpanzees, and monkeys). In certain embodiments, the subjects, e.g., patients, are humans.

Systems

As summarized above, systems for draining a body cavity are also provided. A system as in the subject invention can include a surgical drain configured to drain a body cavity (such as a surgical drain of the invention), and/or a sheath of the invention (such as described above), and a drainage apparatus.

The surgical drain of the subject invention has a lumen which is configured to drain a substance from a body cavity. The surgical drain also has a proximal end which is configured to be outside of the body when the distal end of the surgical drain is present in the body. Therefore, the proximal end of the surgical drain can be attached to a drainage apparatus. By "drainage apparatus" is meant any device or chamber which can be attached to the proximal end of a surgical drain, that can be used to collect a substance drained from the body cavity, e.g., fluid, air, blood, etc. For example, the proximal end of the surgical drain can be attached to any suitable drainage apparatus such as a collection bag or container. The surgical drain can be configured to drain by gravity. The drainage apparatus can also include a valve, such as a flutter valve, or a one-way valve, to prevent body fluids from flowing back into the body, air from leaking in, and also to prevent contamination of the body cavity from the environment.

In some embodiments, when the surgical drain is used in a pleural body cavity, the proximal end of the surgical drain may be attached to a drainage apparatus which includes a "water seal" chamber which acts as a one-way valve. The presence of a water seal allows air and/or fluid to escape from the pleural space, maintains the slightly negative pressure in the pleural space, and prevents any contamination from outside the patient's body. In some embodiments, such as with a surgical drain in the pleural cavity, the proximal end of the surgical drain can be attached to a suction device.

Kits

Also provided are kits that at least include the subject devices. The subject kits at least include a surgical drain or a sheath of the subject invention and instructions for how to use the device in a procedure.

In some embodiments, the kits can include at least one surgical drain. In other embodiments, a set can also include a sheath configured to be disposed around the surgical drain, and instructions for placing the sheath around either a surgical drain of the subject invention, or another suitable sheath. The kits can also include one or more securing devices for attaching a sheath to a surgical drain, such as a clip, a needle and suture, an adhesive, etc. In another embodiment, a drain that may or may not have a sheath attached may be provided with items needed for introducing a surgical drain into a body cavity (e.g., a drain introducer kit) using percutaneous or minimally invasive methods. A drain introducer kit can include implements suitable for inserting a surgical drain or surgical drain and attached sheath into a body cavity, such as an introducer needle, an introducer cannula, a dilator, a guidewire, etc.

In some embodiments, the kits can also include a drainage apparatus, such as a collection bag or container, a valve configured to be attached to the proximal end of the surgical drain, a suction apparatus, etc.

The instructions for using the devices as discussed above are generally recorded on a suitable recording medium. For example, the instructions may be printed on a substrate, such as paper or plastic, etc. As such, the instructions may be present in the kits as a package insert, in the labeling of the container of the kit or components thereof (i.e. associated with the packaging or subpackaging) etc. In other embodiments, the instructions are present as an electronic storage data file present on a suitable computer readable storage medium, e.g., CD-ROM, diskette, etc. The instructions may take any form, including complete instructions for how to use the device or as a website address with which instructions posted on the world wide web may be accessed.

Utility

The present invention describes surgical drains and sheaths that can be used for drainage of body cavities, spaces or organs that functions as a typical surgical drain, tube or cannula, which has the capability of collapsing to a state of reduced diameter. The subject surgical drains can be placed intraoperatively during open procedures or via percutaneous placement via nonguided techniques or guided techniques such as (but not limited to) x-rays, fiberoptic, endoscopic, ultrasonographic or other imaging techniques like magnetic resonance imaging. The device achieves these ends by providing for a significant decrease in drain diameter prior to withdrawal of the device. Access to any body space or organ for various purposes including, but not limited to perfusion, treatment or drainage is possible and where withdrawal of a device with a reduction in diameter is beneficial.

Incorporation of a diameter-varying element mechanism as a part of the invention provides as well for insertion of the drain in a collapsed or non-collapsed state, depending on the preference of the operator. The functioning diameter of the drain can be maintained at a relatively large diameter while the function of the tube (e.g., drainage, perfusion, drug delivery, etc.) The larger functioning diameter is changeable to a smaller diameter for insertion and withdrawal of the drain. The variable diameter is based on the concept of removing the supporting air, gas, liquid, or solid and allowing the reduction of diameter or collapse of the tube or drain prior to insertion or withdrawal. The varying diameter element permits several advantages including but not limited to easier insertion of the drain, easier, less painful withdrawal of the drain, improved surface area of functioning tubing providing drainage, multiple limbs exiting through a single main limb, and drug delivery along the tissue tract.

The collapsible nature of the invention permits several other functions including the use of softer materials which are less likely to injure tissues. Safety is also improved by the collapse of the drain, which decreases the opportunity for iatrogenic introduction of outside air during withdrawal.

In addition to the ability to vary the diameter of the device, the subject surgical drains can also have branches, allowing for wider draining through a single skin incision or opening, without the need for placement of multiple drains. For example, after cardiothoracic surgery, separate drains are often placed into one or both pleural cavities and one or more tubes are often concomitantly placed into the mediastinum or pericardial space. Therefore, patients often experience the discomfort of 3 or 4 indwelling tubes or drains in the chest cavity. This discomfort is then increased by the pain, often despite narcotic administration, of the removal of the multiple drains. For many patients, removal of the tubes is the most painful part of the operative experience and recovery.

The surgical drain can also allow in one embodiment the delivery of pain medication or other desired medication via a drug delivery lumen. Furthermore, by using branches or limbs constructed with malleable tubing or wire, the device permits directivity or malleability of the invention away from delicate structures, yet later when collapsed the invention is withdrawn safely. The invention facilitates wide safer drainage, yet limits the number of skin penetrations, pain, discomfort and scarring while achieving this goal.

The present invention also describes sheaths that can be used with a surgical drain, tube, catheter, or cannula, or other cylindrical structure. The sheath can provide some cushioning effect for any indwelling drain or cannula while it is in place. Also, the sheath can also allow in one embodiment the delivery of pain medication or other desired medication via a drug delivery lumen. Drugs could be administered while the sheath is in place, or they can be used in preparation for the imminent withdrawal procedure. During the actual withdrawal the invention provides a gliding surface for the drain to exit the body and then follows in the collapsed state directly or if attached by the operator to the distal end the invention inverts thus reducing further the friction and pain.

The unique nature of the collapsing drain, tube or cannula enables other features such as ease of insertion of a larger functioning diameter tube in awake patients, multiple drainage branches, adjustable placement of the branches and centralization of the branches into a single drainage lumen exiting the body. The invention facilitates wide safer drainage, yet limits the number of skin penetrations, pain, discomfort and scarring while achieving this goal.

The present invention describes a sheath for shielding the patient or animal from an indwelling drain, tube, catheter, or cannula. The sheath can decrease the pain associated with the placement or withdrawal of surgical drains or other transcutaneous indwelling catheters, tubes or cannulas. The device can also be used with any drains, catheters, tubes, cannula or other cylindrical structures that are inserted into body orifices or tracts. The device acts as a sheath to shield the enclosed drain, catheter, tube or cannula from direct contact with painful nerve endings while the drain, catheter tube or cannula is in place and/or as it is withdrawn. The sheath can allow the full function of the enclosed functioning tube via fenestrations, which allows the device to function. The sheath may also have incorporated in the wall of the sheath another tube or catheter for the administration of medication to treat a pathologic process in the proximity of the device or to pharmacologically decrease the pain of the drain, catheter tube or cannula while indwelling and or upon removal. In some instances, the subject sheath can be secured at the time of manufacture to the proximal end or distal end of the enclosed drain, catheter, tube or cannula. In some embodiments, the subject sheath can be placed at the time of manufacture around an enclosed drain, catheter, tube or cannula, without being secured to the enclosed drain, catheter, tube or cannula. The subject sheath can also be fixed by the operator (e.g., a surgeon) to the proximal end or distal end of the enclosed drain, catheter, tube or cannula, and then in collapsed form the sheath can be removed from the body attached to the previously enclosed drain, catheter, tube or cannula. The sheath may exit directly with the attached drain or catheter, or by inverting, depending upon the method of attachment to the enclosed drain, catheter, tube or cannula.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims. It is also to be understood that the terminology used herein is for the purpose of describing particular embodiments only, and is not intended to be limiting, since the scope of the present invention will be limited only by the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method of draining a pleural body cavity in a body, the method comprising:
   positioning a distal end of an elongated structure in a pleural body cavity, wherein the elongated structure comprises:
   a distal end configured to be placed in the pleural body cavity;

a proximal end configured to be outside of the body when the distal end is present in the pleural body cavity; and a lumen configured to drain a substance from the pleural body cavity and change in inner diameter when present in the pleural body cavity from a first inner diameter to a second inner diameter that is smaller than the first inner diameter, wherein the change in inner diameter is mediated by a diameter-varying element that is present along at least a distal one third of the distal end;

draining the substance from the pleural body cavity via the elongated structure;

decreasing the inner diameter of the distal end of the elongated structure prior to removal of the elongated structure; and removing the distal end of the elongated structure from the pleural body cavity.

2. The method according to claim 1, wherein the decreasing comprises removing the diameter-varying element from the elongated structure.

3. The method according to claim 2, wherein the diameter-varying element is a wire.

4. The method according to claim 1, wherein the method further comprises removing a tubular structure disposed around an outer surface of the elongated structure, wherein the tubular structure is secured to the distal end of the elongated structure, such that the tubular structure is removed after the elongated structure has been removed.

5. The method according to claim 1, wherein the method further comprises removing a tubular structure disposed around an outer surface of the elongated structure, wherein the tubular structure is secured to the proximal end of the elongated structure, such that the tubular structure is removed at the same time as the elongated structure is removed.

6. The method according to claim 1, wherein the position comprises inserting the distal end of the elongated structure through an incision in the skin of the body.

7. The method according to claim 1, wherein the substance comprises air and liquid.

8. The method according to claim 1, wherein the positioning is performed when the inner diameter is the second inner diameter.

9. The method according to claim 1, wherein the change in inner diameter from the first inner diameter to the second inner diameter is 50% or more.

10. The method according to claim 1, wherein the elongated structure comprises two or more branches.

11. A method of draining a thoracic body cavity in a body, the method comprising:

positioning a distal end of an elongated structure in a thoracic body cavity, wherein the elongated structure comprises:

a distal end configured to be placed in a thoracic body cavity;

a proximal end configured to be outside of the body when the distal end is present in the thoracic body cavity; and a lumen configured to drain a substance from the thoracic body cavity and change in inner diameter when present in the thoracic body cavity from a first inner diameter to a second inner diameter that is smaller than the first inner diameter, wherein the change in inner diameter is mediated by a diameter-varying element;

draining the substance from the thoracic body cavity via the elongated structure;

decreasing the inner diameter of the distal end of the elongated structure prior to removal of the elongated structure; and removing the distal end of the elongated structure from the thoracic body cavity.

12. The method according to claim 11, wherein the decreasing comprises removing the diameter-varying element from the elongated structure.

13. The method according to claim 12, wherein the diameter-varying element is a wire.

14. The method according to claim 12, wherein the diameter-varying element is a central spline.

15. The method according to claim 11, wherein the method further comprises removing a tubular structure disposed around an outer surface of the elongated structure, wherein the tubular structure is secured to the distal end of the elongated structure, such that the tubular structure is removed after the elongated structure has been removed.

16. The method according to claim 11, wherein the method further comprises removing a tubular structure disposed around an outer surface of the elongated structure, wherein the tubular structure is secured to the proximal end of the elongated structure, such that the tubular structure is removed at the same time as the elongated structure is removed.

17. The method according to claim 11, wherein the thoracic body cavity is a pericardial body cavity.

18. The method according to claim 11, wherein the positioning is performed when the inner diameter is the second inner diameter.

19. The method according to claim 11, wherein the change in inner diameter from the first inner diameter to the second inner diameter is 50% or more.

20. The method according to claim 11, wherein the elongated structure comprises two or more branches.

* * * * *